United States Patent [19]

Hurlimann et al.

[11] Patent Number: 5,680,043

[45] Date of Patent: Oct. 21, 1997

[54] NUCLEAR MAGNETIC RESONANCE TECHNIQUE FOR DETERMINING GAS EFFECT WITH BOREHOLE LOGGING TOOLS

[75] Inventors: Martin D. Hurlimann; Robert L. Kleinberg, both of Ridgefield, Conn.

[73] Assignee: Schlumberger Technology Corporation, Ridgefield, Conn.

[21] Appl. No.: 409,299

[22] Filed: Mar. 23, 1995

[51] Int. Cl.$^6$ .................................................. G01V 3/14
[52] U.S. Cl. ......................................................... 324/303
[58] Field of Search ................................. 324/300, 306, 324/307, 309, 316, 318, 303; 128/653.2, 653.5

[56] References Cited

U.S. PATENT DOCUMENTS

| | | | |
|---|---|---|---|
| 4,714,881 | 12/1987 | Givens | 324/303 |
| 4,719,423 | 1/1988 | Vinegar et al. | 324/303 |
| 4,933,638 | 6/1990 | Kenyon et al. | 324/303 |
| 5,023,551 | 6/1991 | Kleinberg et al. | 324/303 |
| 5,055,787 | 10/1991 | Kleinberg et al. | 324/303 |
| 5,055,788 | 10/1991 | Kleinberg et al. | 324/303 |
| 5,212,447 | 5/1993 | Paltiel | 324/300 |
| 5,280,243 | 1/1994 | Miller | 324/303 |
| 5,289,124 | 2/1994 | Jerosch-Herold et al. | 324/303 |
| 5,291,137 | 3/1994 | Freedman | 324/303 |
| 5,309,098 | 5/1994 | Coates et al. | 324/303 |
| 5,363,041 | 11/1994 | Sezginer | 324/303 |
| 5,387,865 | 2/1995 | Jerosch-Herold et al. | 324/303 |
| 5,389,877 | 2/1995 | Sezginer et al. | 324/303 |
| 5,486,762 | 1/1996 | Freedman et al. | 324/303 |
| 5,498,960 | 3/1996 | Vinegar et al. | 324/303 |

FOREIGN PATENT DOCUMENTS 0 489 578 A1  10/1992  European Pat. Off. .......... G01V 3/32

OTHER PUBLICATIONS

Butler et al., "Estimating Solutions of First Kind Integral Equations with Non-Negative Constraints and Optimal Smoothing", *SIAM Journal of Numerical Anaylsis*, vol. 18, No. 3, Jun. 1981.

A. Sezginer, R. L. Kleinberg, M. Fukuhara, and L. L. Latour, "Very Rapid Simultenous Measurement of Nuclear Magnetic Resonance Spin–Lattice Relaxation Time and Spin–Spin Relaxation Time", *Journal of Magnetic Resonance*, vol. 92, pp. 504–527, 1991.

R. Akkurt, H. J. Vinegar, P. N. Tutunjian, and A. J. Guillory, "NMR Logging of Natural Gas Reservoirs", SPWLA 36th Annual Logging Symposium, Jun. 26–29, 1995, pp. 1–12.

*Primary Examiner*—Sandra L. O'Shea
*Assistant Examiner*—Roger Phillips
*Attorney, Agent, or Firm*—Leonard W. Pojunas; Brigitte L. Jeffery; Keith G. W. Smith

[57] ABSTRACT

An NMR pulse sequence technique for use in the borehole environment is provided which uses CPMG pulses according to $$[W_i-90-(t_{cp}-180-t_{cp}-echo)_j]_i$$

where j is the index of the CPMG echoes gathered, i is the index of the wait times in the pulse sequence, $W_i$ are the varying wait times before the CPMG pulses, and tcp is the Carr-Purcell spacing. Measurements are made of the signals induced in the formation as a result of the magnetic fields to find the spin-echo relaxation time T1. Using T1, the gas effect on formation parameters may be derived. Also, gas saturation and gas chemical composition can be derived. In addition, the diffusion coefficient of gas under reservoir conditions can be more than ten times larger than that of water, making the $T_2$ relaxation time of gas more sensitive to static magnetic field gradients. In formations where gas occupies pores larger than about 10 μm, this $T_2$ effect (effect of diffusion on the measured $T_2$ relaxation times of gas) can be used to identify gas even though the tool gradients are not uniform.

32 Claims, 11 Drawing Sheets

NUCLEAR MAGNETIC RESONANCE TECHNIQUE FOR DETERMINING GAS EFFECT WITH BOREHOLE LOGGING TOOLS

FIELD OF THE INVENTION

This invention generally relates to nuclear magnetic resonance (NMR) techniques useful in the evaluation of earth formations. More particularly, the invention relates to NMR techniques which may be used by a nuclear magnetic resonance logging tool for measuring earth formation properties such as the gas effect on porosity, permeability, and saturation.

BACKGROUND OF THE INVENTION

Nuclear magnetic logging tools such as disclosed in U.S. Pat. Nos. 5,055,787, and 5,055,788, and also disclosed inter alia in the specification of U.S. Pat. No. 4,933,638, measure the number and nuclear magnetic relaxation rates of hydrogen atoms in the pore space of rocks by measuring the amplitude and decay rate of signals resulting from pulse sequences. One example of such a tool is the "CMR" (Combined Magnetic Resonance) Tool, mark of Schlumberger. In essence, the nuclear magnetic logging tools send a stream of pulses into the formation and monitor the returning echoes. The measurements made are typically cyclical, with each cycle taking several seconds. Interpretation algorithms are then used to find the formation properties of interest.

Measurable Formation Properties

The strength of the nuclear magnetic signal is directly proportional to the number of resonated "spins" of nuclei present in the examined volume of an earth formation. NMR tools can be tuned in frequency to resonate a particular nuclear species. Hydrogen is the nucleus of choice in most borehole measurements. The number of hydrogen atoms in the formation in turn is related to fluid (e.g., gas, water, oil) filled porosity. The signal amplitude of a tuned tool measures the number of hydrogen atoms in the formation. In addition to being sensitive to hydrogen density, nuclear magnetism tools are sensitive to the environment (e.g., earth formation) of the hydrogen being examined. Hydrogen in a bound or "irreducible" fluid typically has a spin-lattice relaxation time (T1) of milliseconds to tens of milliseconds, while free or producible fluid has a T1 in the range of tens to hundreds of milliseconds. Hydrogen bound in the minerals of a solid matrix, such as gypsum, has a long T1, (several seconds or longer), but has a very short T2 spin-spin relaxation time, so it is invisible to measurement tools. Thus, the decaying NMR signals received by the nuclear magnetic tools are not corrupted by the hydrogen of the solid matrix. A typical borehole nuclear magnetic logging tool does not have a short enough deadtime to detect a spin-spin relaxation time signal from the solid matrix. Rather, the NMR tool can detect all fluid protons or "spins" which are indicative of the fluid filled porosity of the formation. NMR measurement of total porosity is described in U.S. Pat. Nos. 5,363,041 and 5,389,877 to Sezginer and Sezginer et al., respectively.

Besides correlating well to porosity, the measurements resulting from the NMR sequences applied to the formation provide information which may be correlated with the "free fluid index", permeability, and residual oil saturation. A number of transforms have been introduced to determine permeability by well logs. See U.S. Pat. No. 5,023,551 to Kleinberg et al., patented Jun. 11, 1991, Col. 2, line 9–Col. 3, line 20, for example.

Viewed as a multi-exponential decay curve, rock NMR data can be used to quantitatively measure the amounts of immovable fluid (fast relaxing component) and movable fluid (slow relaxing component). The latter is of tremendous importance in the evaluation of oil reservoirs, because it is only the movable fluid that can be produced from a well.

Principles of NMR and Pulse Sequences

NMR is based on the fact that the nuclei of many elements have angular momentum ("spin") and a magnetic moment. The nuclear spins align themselves along an externally applied static magnetic field. This equilibrium situation can be disturbed by a pulse of an oscillating magnetic field, which tips the spins away from the static field direction. The angle through which the spins are tipped is under the control of the experimenter, as explained below.

After tipping, two things occur simultaneously. First, the spins precess around the static field at a particular frequency (i.e., the Larmor frequency), given by $\omega_o = \gamma B_o$ where $B_o$ is the strength of the static field and $\gamma$ is the gyromagnetic ratio, a nuclear constant. Second, the spins return to the equilibrium direction according to a decay time known as the "spin-lattice relaxation time" or T1. For hydrogen nuclei, $\gamma/2\pi = 4258$ Hz/Gauss. So for a static field of 235 Gauss, the frequency of precession is 1 MHz. T1 is controlled totally by the molecular environment and is typically ten to one thousand milliseconds for water in rocks.

Also associated with the spin of molecular nuclei is a second relaxation time known as the "spin-spin relaxation time" or T2. At the end of a ninety degree tipping pulse, all the spins are pointed in a common direction perpendicular to the static field, and they all precess at the Larmor frequency. However, because of small inhomogeneities in the static field due to imperfect instrumentation or microscopic material heterogeneities, each nuclear spin precesses at a slightly different rate. Hence, after a time long compared to the precession period, but shorter than T1, the spins will no longer be precessing in unison. When this dephasing is due to static field inhomogeneity of the apparatus, the dephasing is called T2*. When it is due to properties of the material, the dephasing time is called T2. T2 and T2* can be measured independently. For water in rocks, T2 is approximately one-half of T1.

Again, the parameters T1 and T2 are sensitive to molecular environment. For example, T2 can be several seconds in an unconfined low viscosity liquid such as water, while it can be as short as ten microseconds in a solid. Liquids confined in the pores of rocks present an intermediate case with T2 in the range of tens to hundreds of milliseconds, depending on pore size and fluid viscosity.

In the basic NMR measurement, a pulse of oscillating field is applied to the sample to tip the spins of the nuclei in the sample. The angle (in radians) through which the spins are tipped is given by the equation $$\theta = \gamma B_1 t_p / 2$$

where $\gamma$ is the gyromagnetic ratio, $B_1$ is the linearly polarized oscillating field strength, and $t_p$ is the duration of the pulse. Tipping pulses of ninety and one hundred and eighty degrees are the most common.

The precessing spins are detected by voltage induced in an antenna or coil. Only that component of the nuclear magnetization that is precessing in the plane perpendicular to the static field can be sensed by the antenna. Hence, a signal will be generated after a ninety degree tipping pulse but not after a one hundred eighty degree tipping pulse. In fact, after a one hundred eighty degree tipping pulse, the spins do not precess at all, but just slowly return along the $B_o$ axis to the equilibrium direction.

A standard method known as the CPMG sequence (CarrPurcell-Meiboom-Gill) for measuring T2 has evolved. In solids, where T2 is very short, T2 can be determined from the decay of the detected signal after a ninety degree pulse. However, for liquids where $T2^* \ll T2$, the free induction decay becomes a measurement of the apparatus-induced inhomogeneities. To measure the true T2 in such situations, it is necessary to cancel the effect of the apparatus-induced inhomogeneities. To accomplish the same, a series of pulses is applied. First a ninety degree pulse causes the spins to start precessing. Then a one hundred eighty degree pulse is applied to keep the spins in the measurement plane, but to cause the spins which are dispersing in the transverse plane to reverse direction and to refocus. By repeatedly reversing the spins by one hundred eighty degree pulses, a series of "spin echoes" occur. This succession of one hundred eighty degree pulses after an initial ninety degree pulse is the Carr-Purcell sequence which measures the irreversible dephasing (i.e., T2) due to material properties. Meiboom and Gill devised a modification to the Carr-Purcell pulse sequence such that after the spins are tipped by ninety degrees and start to dephase, the carrier of the one hundred eighty degree pulses is phase shifted relative to the carrier of the ninety degree pulse. As a result, any error that occurs during an even pulse of the CPMG sequence is cancelled out by an opposing error in the odd pulse.

A detailed explanation of NMR principles and pulse sequences is described in U.S. Pat. No. 5,291,137 to Freedman.

SUMMARY OF THE INVENTION

The invention involves an apparatus and method for evaluating an earth formation using a nuclear magnetic resonance (NMR) tool. The steps of the method comprise: producing a static magnetic field in the formation; producing an oscillating magnetic field in the formation according to a pulse sequence having at least one of the SET: {waiting time, recovery time, and pulse spacing}; varying at least one of the SET of a subsequent pulse sequence; receiving resulting signals induced in the formation; and indicating a gas attribute of the formation discernible in response to varying at least one of the SET.

According to one embodiment of the invention, the borehole tool produces a static magnetic field and an oscillating magnetic field in the formation. The oscillating field is produced according to a pulse sequence having a time parameter which is varied, changing the pulse sequence. Such variable time parameters are $W_i$ waiting time, and pulse spacing $t_{cp}$(half the time between echoes) in the CPMG pulse sequence. In addition to $W_i$ and $t_{cp}$, another variable time parameter is the recovery time, $\tau_i$, in the fast inversion recovery (FIR) CPMG sequence. It is only necessary to vary one time parameter of the set: {waiting time, recovery time, pulse spacing} to indicate a gas attribute of the formation. After receiving resulting signals induced in the formation, the gas attribute is indicated based on such received signals. The gas attribute is discernible in response to varying at least one time parameter of the set. "$t_{cp}$" is the time between the first 90 degree pulse and the 180 degree pulse. One uses "$T_E$" to indicate the time between subsequent echoes. This is also the time between two 180 degree pulses. The relationship between "$t_{cp}$" and "$T_E$" is usually, TE+2*tcp. However there need be no particular relationship, if desired. For the purposes of this application, $T_E$ (echo spacing) and $t_{cp}$ (pulse spacing) are to be considered independent and different values.

The invention also concerns an apparatus and a method for indicating an attribute of an earth formation using a nuclear magnetic resonance tool comprising: producing a static magnetic field in the formation; producing an oscillating magnetic field in the formation according to at least a first pulse sequence having a first timing pattern, and a second pulse sequence having a second timing pattern different from the first timing pattern; receiving resulting signals induced in the formation in response to the first and second pulse sequences; and indicating a gas attribute of the formation based on the received, induced signals.

According to another embodiment, the oscillating magnetic field in the formation is produced according to first and second pulse sequences having different first and second timing patterns, respectively. The different timing pattern involve at least one different time period between pulses. Resulting signals induced in the formation are received. A gas attribute of the formation is determined, based on the received signals. The gas attribute of the formation which is attained according to this invention is used to calculate total porosity, to indicate gas saturation.

In particular, a borehole tool such as described in U.S. Pat. Nos. 5,055,787, and 5,055,788 is placed down a borehole traversing a formation, and a volume of the formation is subjected to a static magnetic field and to an oscillating magnetic field which is controlled according to a pulse sequence which permits simultaneous measurement of T1 and T2. The preferred pulse sequence is:

$$[W_i-90-(t_{cp}-180-t_{cp}-echo)_j]_i$$

where j=1, 2 ... J, where J is the number of echoes collected in the CPMG sequence and is typically on the order of hundreds to thousands; i=1, 2, ... I, where I is the number of recovery times; $W_i$ are waiting times; and $t_{cp}$ is the Carr-Purcell spacing. Measurements of the signals induced in the formation as a result of the magnetic fields are made of each of a predetermined number of echoes. In one embodiment, each echo measurement of the CPMG sequence is a measurement of the integrated amplitude of the echo, rather than a measurement of the greatest amplitude of the received echo. Determinations of T1, T2, and amplitude (Mo) can then be made from the measurements. From one or more of the T1, T2, and amplitude determinations, formation parameters such as porosity and permeability may be derived according to equations known in the art.

Additional objects and advantages will become apparent to those skilled in the art upon reference to the detailed description taken in conjunction with the provided Figures.

DETAILED DESCRIPTION OF THE PREFERRED EMBODIMENT

Figure 1:
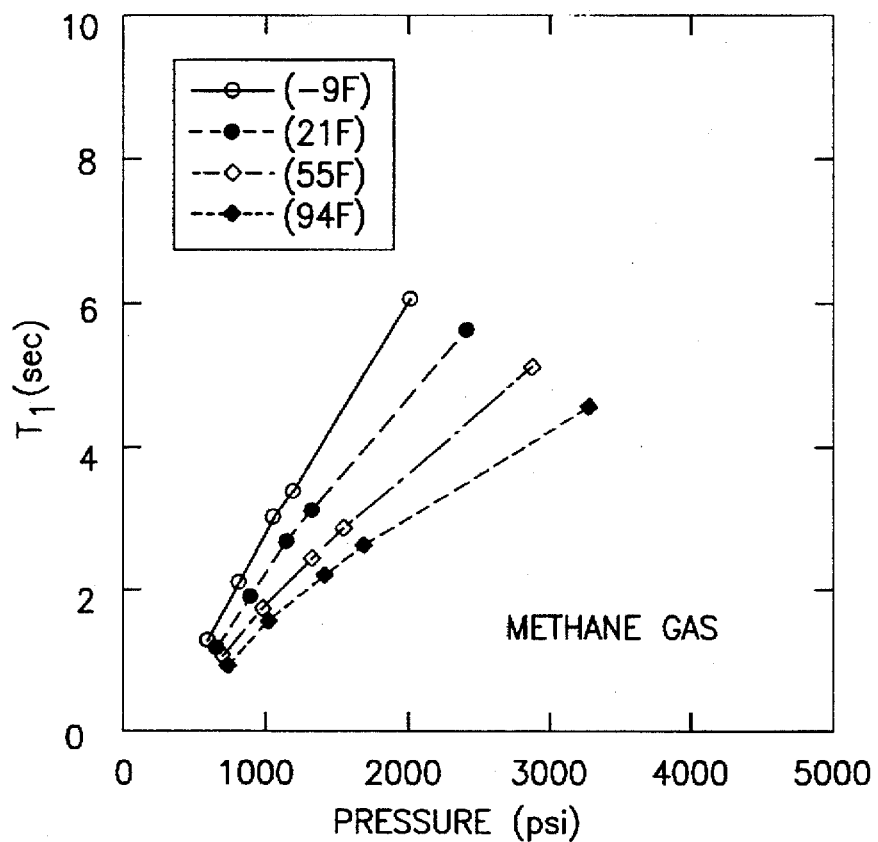
FIG. 1 shows T1 plotted as a function of pressure for Methane gas.

Below, techniques for determining an attribute of gas in various types of hydrocarbon reservoirs are described. First, the basic physics of the NMR relaxation times is described. Then the various types of reservoirs are delineated, and methods are given for determining gas content in each type by manipulating waiting times and examining T1 and/or T2. Then, reduced $T_2$ relaxation times due to diffusion, or the gas effect in NMR, is described. Pulse spacings are manipulated and T2 is examined to see the gas effect.

Formation liquids are usually not characterized by simple exponential NMR decays. In other words, their NMR relaxations are multiexponential. Usually oil and water are characterized by a distribution of relaxation times. In contrast, gas is characterized by its bulk relaxation rate, and its NMR decay has a simple exponential character with a single relaxation time.

Contributions to $T_1$

For any fluid in the pores of a rock, there are two contributions to $T_1$:

$$1/T_1 = (1/T_1)b + (1/T_1)s \quad (1)$$

The first contribution is the bulk relaxation of the fluid. This is the relaxation that occurs in the absence of rock, and its rate is unaffected by rock properties. The second contribution is the relaxation that occurs when fluid molecules diffuse to the grain surfaces, and are relaxed there by interactions with the solid surface.

For a water-wet rock, the rate of relaxation of the water is the sum of the first and second contributions, whereas oil or gas in the rock relax at their bulk relaxation rate. Oil and gas are prevented from interacting with the surface by the water. There is no significant enhancement of relaxation at a hydrocarbon-water surface.

For an oil-wet rock, the rate of relaxation of the oil is the sum of the first and second contributions, whereas water or gas in the rock relax at their bulk relaxation rate.

In both these cases, gas is unable to reach the surface and therefore relaxes at its bulk relaxation rate.

Contributions to $T_2$ $T_2$ relaxation of any fluid in a rock is caused by three mechanisms working simultaneously in parallel:

$$1/T_2 = (1/T_2)b + (1/T_2)s + (1/T_2)d \quad (2)$$

The first is the bulk fluid relaxation, a property of the fluid itself, unaffected by its presence in the rock. $T_2$(bulk) of gases such as methane and ethane is equal to their $T_1$(bulk). The second is the relaxation resulting from an encounter with grain surfaces. As explained above, gas is not expected to relax at grain surfaces, because the water or oil film acts as a protective barrier. The third is relaxation when the molecules diffuse in a magnetic field gradient. This is discussed below in detail in "Gas Effect: Enhanced $T_2$ Relaxation Due to Diffusion".

Gas Detection from Longitudinal Relaxation Time $T_1$: Simple Exponential Relaxation of Each Fluid If the NMR relaxation of formation fluids can be characterized by simple exponential decays, and if the longitudinal relaxation times of water, oil and gas are, respectively, $T_{1w}$, $T_{1o}$, $T_{1g}$, the longitudinal decay of magnetization as determined by an inversion recovery experiment [see e.g. Sezginer et al, Journal of Magnetic Resonance 92, 504–527 (1991)] is $$S(t,W \to \infty) = (\alpha)*\phi*S_w*HI_w*[1-2exp(-t/T_{1w})] + (\alpha)*\phi*S_o*HI_o*[1-2exp(-t/T_{1o})] + (\alpha)*\phi*S_g*HI_g*[1-2exp(-t/T_{1g})] \quad (3)$$

$\alpha$ is a tool calibration constant, $\phi$ is the formation porosity, $S_w$, $S_o$, and $S_g$ are the saturations of water, oil, and gas respectively, and $HI_w$, $HI_o$, $HI_g$ are the hydrogen indices of water, oil, and gas, respectively.

There are many other ways of measuring $T_1$, as described by Sezginer et al, Journal of Magnetic Resonance 92, 504–527 (1991), and by Kleinberg et al, U.S. Pat. No. 5,023,551. Any of these methods can be used.

The wait time W is the time between the end of one inversion recovery pulse sequence and the start of the next. For Eqn. (3) to be valid, the wait time must be much longer than the longitudinal relaxation time of all formation fluids. If the wait time does not satisfy the criterion $W >> T_{1w}, T_{1o}, T_{1g}$ then the signal is reduced according to the formula $$S(t,W) = (\alpha)*(\phi*S_w*HI_w)*[1-(2-exp(-W/T_{1w}))exp(-t/T_{1w})] + (\alpha)*(\phi*S_o*HI_o)*[1-(2-exp(-W/T_{1o}))exp(-t/T_{1o})] + (\alpha)*(\phi*S_g*HI_g)*[1-(2-exp(-W/T_{1g}))exp(-t/T_{1g})] \quad (4)$$

The relaxation time $T_1$ of water in water-wet rocks is usually in the range 0.01 sec to 1 sec. The relaxation time of crude oils found in reservoirs is usually in the same range. In contrast, gas has a relatively long $T_1$, see FIG. 1. For example, for 200° F. and 4000 psi, typical of some North American gas fields, $T_1$ of methane is about 3 sec. $T_1$ increases with pressure and decreases with temperature. $T_1$ of the gas is unaffected by the formation because gas cannot come in contact with grain surfaces in water wet rocks.

There is a case where a gas signal can be confused with a water signal. In hot vuggy carbonates, $T_{1w}$ can equal or exceed $T_{1g}$. In that case, gas cannot be distinguished from water based on $T_1$ alone. However, in that case $T_2$ methods can be effective, as explained in below "Gas Effect: Enhanced $T_2$ Relaxation Due to Diffusion". The choice of method to be used is also explained below.

The most convenient way to analyze NMR decays expressed by Eqn. (4) is to convert S(t,W) into a $T_1$ spectrum $P(T_1)$. Means for performing this operation are discussed by J. P. Buffer, J. A. Reeds, and S. V. Dawson in "Estimating Solutions of First Kind Integral Equations with Nonnegative Constraints and Optimal Smoothing", SIAM J. Numer. Anal. 18, 381–397 (June 1981).

To quantify the amount of gas in a formation, the following procedure can be used:

1. Log the formation using any sequence appropriate for measuring $T_1$.
2. Determine the function $S(t)$ at each depth.
3. Convert each $S(t)$ into a $T_1$ spectrum, $P(T_1)$.
4. Select the component of the spectrum $P(T_1)$ that corresponds to the $T_1$ of the gas signal, which is known from the temperature, pressure, and composition of the gas. The result is $$P(T_{1g}) = \phi * S_g * HI_g \tag{5}$$

5. Determine $\phi$ as explained below, or from other logs. From the temperature, pressure, and gas composition, determine the hydrogen index of the gas, $HI_g$. Knowing these, the gas saturation $S_g$ can be determined.

Effect of Multiexponential NMR Relaxation

Formation liquids are usually not characterized by simple exponential NMR decays. In other words, their NMR relaxations are multiexponential. Usually oil and water are characterized by a distribution of relaxation times. In contrast, gas is characterized by its bulk relaxation rate, and its NMR decay has a simple exponential character with a single relaxation time.

In the presence of finite signal to noise ratio, the spectrum associated with each fluid is broadened. Thus even single exponential decays are represented by a $T_1$ spectrum, though of a relatively narrow width.

The decay of longitudinal magnetization as determined by a fast inversion recovery measurement is a summation of signals from water, oil, and gas fractions of the pore fluid:

$$S(t,W) = (\alpha) \sum_i (\phi * S_w * HI_w)_i * [1 - (2 - \exp(-W/T_{1wi}))\exp(-t/T_{1wi})] + \tag{6}$$
$$(\alpha) \sum_i (\phi * S_o * HI_o)_i * [1 - (2 - \exp(-W/T_{1oi}))\exp(-t/T_{1oi})] +$$
$$(\alpha) \sum_i (\phi * S_g * HI_g)_i * [1 - (2 - \exp(-W/T_{1gi}))\exp(-t/T_{1gi})]$$

where $(\phi * S_w * HI_w)_i$, for example, is the fraction of the water that relaxes with time constant $T_{1wi}$.

$P(T_{1i})$ is that part of the received NMR signal that relaxes with longitudinal relaxation time $T_{1i}$, $$P(T_{1i}) \propto [(\phi * S_w * HI_w)_i + (\phi * S_o * HI_o)_i + (\phi * S_g * HI_g)_i] \tag{7}$$

The total gas signal, for example, is $$\phi * S_g * HI_g = \sum_i (\phi * S_g * HI_g)_i \tag{8}$$

where the summation is over that range of $T_{1i}$ around $T_{1gi}$ over which the gas signal is distributed.

When the $T_1$ spectrum can be measured, the quantity of gas can be found by using the following method:

1. Log the formation using any sequence appropriate for measuring $T_1$.
2. Determine the function $S(t,W)$ at each depth.
3. Convert each $S(t,W)$ into a $T_1$ spectrum, $P(T_1)$.
4. Select the range of the spectrum $P(T_1)$ that corresponds to the range of $T_1$ of the gas signal, which is known from the temperature, pressure, and composition of the gas. The result is $$\sum_{gas} P(T_1) = \phi * S_g * HI_g \tag{9}$$

Hybrid $T_1/T_2$ Method

The above methods are suitable when the $T_1$ spectrum is available. Frequently, this is not the case: often only the $T_2$ spectrum, $P(T_2)$, is measured by borehole logging tools. As explained above in the context of the $T_1$ measurement, the $T_2$ signal may be composed of a distribution of relaxation times from each of the water and oil phases. In addition, the $P(T_2)$ of the gas phase may be comprised of a distribution of relaxation times. Unlike $T_{1g}$, $T_{2g}$ may depend on the microgeometry and internal magnetic field gradients of the rock, as explained below in "Gas Effect: Enhanced $T_2$ Relaxation Due to Diffusion"; $P(T_2)$ for gas may be broadened by variabilities of these rock properties, by nonuniform magnetic field gradients of the tool, and by the signal processing algorithm used to transform the magnetization decay into a $T_2$ spectrum.

Because the gas response may overlay water and oil responses in the $T_2$ spectrum, the best way to determine the quantity of gas is to exploit the constancy and large value of $T_1$, even when measuring $T_2$. The best ways to do this are explained under "Method I", below.

The decay of transverse magnetization, as measured by a CPMG sequence, for a formation with gas, oil and water is $$S(t,W) = \alpha \sum_i (\phi * S_w * HI_w)_i * \exp(-t/T_{2wi}) * [1 - \exp(-W/T_{1wi})] + \tag{10}$$
$$\alpha \sum_i (\phi * S_o * HI_o)_i * \exp(-t/T_{2oi}) * [1 - \exp(-W/T_{1oi})] +$$
$$\alpha \sum_i (\phi * S_g * HI_g)_i * \exp(-t/T_{2gi}) * [1 - \exp(-W/T_{1gi})]\}$$

Note that this is significantly more complicated than the expression for the $T_1$ measurement because it depends on both $T_1$ and $T_2$.

A simplification can be obtained by considering the $T_2$ spectrum, similar to the $T_1$ spectrum discussed earlier. The $T_2$ spectrum can be obtained from measurement data by using the methods of Butler, Reeds and Dawson, or by those of Freedman (U.S. Pat. No. 5,291,137). The $T_2$ spectrum that is derived from Equation (10) is $$P(T_{2i}, W) = \alpha * (\phi * S_w * HI_w)_i * [1 - \exp(-W/T_{1wi})] + \alpha * (\phi * S_o * HI_o)_i * [1 - \exp(-W/T_{1oi})] + \alpha * (\phi * S_g * HI_g)_i * [1 - \exp(W/T_{1gi})] \tag{11}$$

where $T_{1wi}$, $T_{1oi}$, $T_{1gi}$ are the $T_1$'s for the fractions of water, oil, and gas, respectively, that have a transverse relaxation time $T_{2i}$.

There are two ways in which Equation (11) can be simplified.

First, for typical values of W used in well logging, the wait time corrections $[1-\exp(-W/T_{1w})]$ and $[1-\exp(-W/T_{1o})]$ are usually small because $T_1$ of water or oil in rocks is frequently in the range 0.01 sec–1 sec, while W is usually selected to be longer than 1 sec. W is 1.3 sec in sandstone depth mode and 2.6 sec in carbonate depth mode for the CMR borehole logging tool.

Second, Equation (11) is considerably simplified if there are known relationships between $T_2$ and $T_1$ for oil, water, and gas. The needed relationships have been discovered empirically. It has been shown that for water in rocks, $T_{1w} \approx 1.65 * T_{2w}$, and for oils, $T_{1o} \approx 1.22 * T_{2o}$. For gas, $T_{1g}$ is independent of $T_{2g}$ and depends only on formation temperature and pressure, see FIG. 1.

Typing of Reservoirs for the Purpose of Gas Quantitation

Selection of the method used to quantify gas is based on the relaxation time of the formation, and to a lesser extent the lithology.

Type I sandstone formations are characterized by pores smaller than 10 μm in radius and NMR relaxation time $T_2 < 1$ sec. This is a well-defined group because small pores and short NMR relaxation times are highly correlated. In the water leg of a Type I formation, $T_2$ is related to pore size through the relation $$(V/S) = \rho_2 T_2 \qquad (12)$$

where V/S is the ratio of the volume of a pore to its surface area. For an arbitrary ellipsoidal pore (three unequal axes) V/S is approximately the shortest radius. For sandstones, the best current value of $\rho_2$ is $\rho_2 = 10$ μm/s. Thus pores with $T_2 < 1$ sec are expected to have smallest radii less than 10 μm. Shaly sands are always Type I.

Type I carbonate formations have $T_2 < 1$ sec. For carbonates, the surface relaxivity $\rho_2$ is about a factor of three smaller than for sandstones. Thus, Type I carbonate formations have minimum pore radii less than 3 μm.

For water in Type I formations, it has been found that generally $T_1/T_2 \sim 1.65$, as noted above.

Type II formations have large pores and long relaxation times. In Type II formations, pores are larger than 10 μm. That implies that for sandstones $T_2 > 1$ sec and for carbonates $T_2 > 3$ sec. Vuggy carbonates are always Type II.

Type III formations are carbonate formations for which $P(T_2)$ is predominantly in the range 1 sec $< T_2 < 3$ sec. In these formations the pores are predominantly smaller than 10 μm, so that varying the echo spacing, $T_E$, fails to distinguish gas from water, see "Gas Effect in NMR: Reduced $T_2$ Relaxation Times Due to Diffusion" below. In these formations $T_1$ for water is in the range 1.5 sec to 5 sec. Thus, varying the wait time, W, also fails to distinguish gas from water. The best way to deal with these formations is to introduce paramagnetic ions such as iron or manganese ions into the mud filtrate, which replaces the original (connate) water in the formation. Paramagnetic ions reduce both $T_1$ and $T_2$ of the water to low values, but do not affect the relaxation times of the gas. Then, gas can be distinguished from water by varying the wait time.

Selection of Method for Quantifying Gas in Subsurface Earth Formations

1. Measure $T_2$ spectrum in water leg of formation

OR

1. Measure $T_2$ spectrum of representative core sample that is fully saturated with water.

OR

1. Determine lithology from other logs.
2. If for the main part of the spectrum $T_2 < 1$ sec, use Method I. If for the main part of the spectrum $T_2 > 1$ sec, use Method II or III.

OR

2. If the formation is known from other logs to be a shaly sand, use Method I.

OR

2. If the formation is known from other logs to be a vuggy carbonate, use Method II or III.
3. If the formation is a carbonate for which much of the weight of $P(T_2)$ is in the range 1 sec $< T_2 < 3$ sec, use Method III.

Method I Flow Chart

Figure 2A:
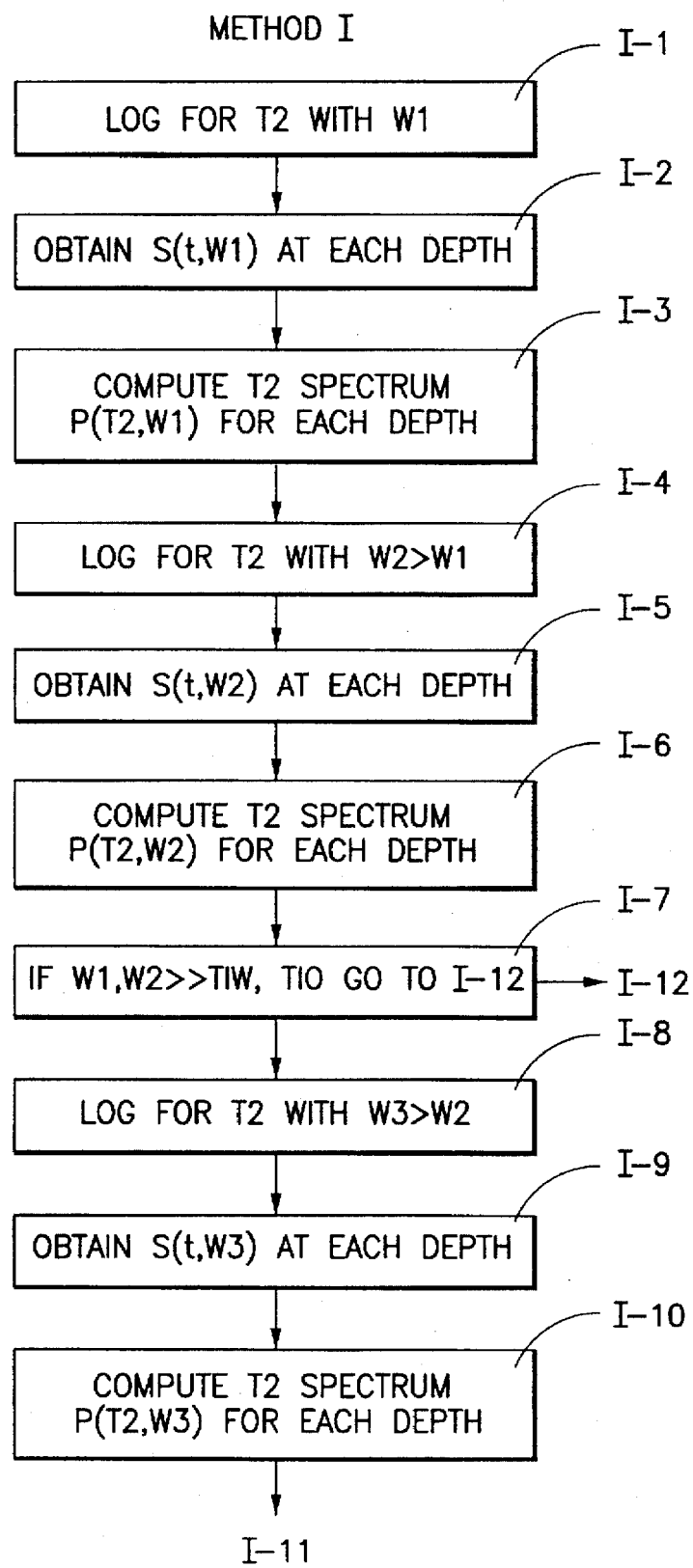
FIGS. 2a, 2b, 3 and 4 illustrate methods for quantifying gas in earth formations.
Figure 2B:
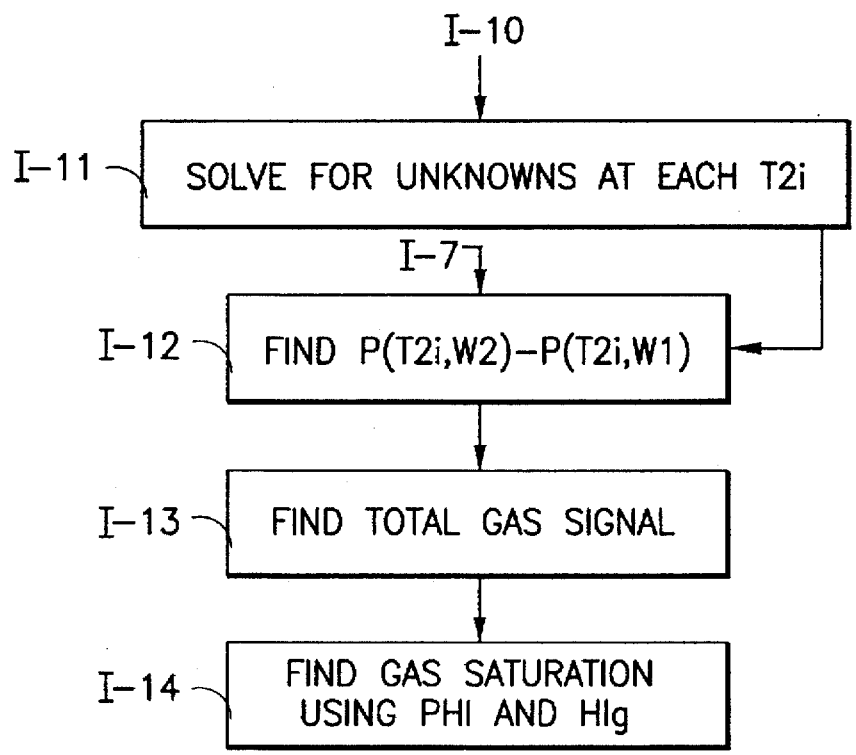

FIGS. 2a and 2b illustrate this method.

I-1. Log the formation for $T_2$ using a wait time $W_1$. The shortest possible echo spacing $T_E$ is preferably used.

I-2. Obtain the signal $S(t, W_1)$ at each depth.

I-3. Compute the $T_2$ spectrum $P(T_2, W_1)$ for each depth.

I-4. Log the formation using a wait time $W_2$ which is longer than $W_1$. Preferably, $T_{1w}, T_{1o} < W_2 < T_{1g}$.

I-5. Obtain the signal $S(t, W_2)$ at each depth.

I-6. Compute the $T_2$ spectrum $P(T_2, W_2)$ for each depth.

I-7. If it is known that $W_1, W_2 >> T_{1w}, T_{1o}$, go to step I-12.

I-8. Log the formation using a wait time $W_3$ which is longer than $W_2$. $W_3$ is preferably comparable to or longer than $T_{1g}$.

I-9. Obtain the signal $S(t, W_3)$ at each depth.

I-10. Compute the $T_2$ spectrum $P(T_2, W_3)$ for each depth.

Note that it is possible to acquire logs for $W_1$, $W_2$, and $W_3$ in an interleaved manner, so that only a single logging pass is required.

For each value of $T_2$ in the spectrum $P(T_2)$ there are now three measurements and three unknowns. The equations to be solved are $$P(T_{2i}, W_j) = \alpha*(\phi*S_w*HI_w)_i*[1 - exp(-W_j/(1.65*T_{2i})] + \alpha*(\phi*S_o*HI_o)_i* [1 - exp(-W_j/(1.22*T_{2i})] + \alpha*(\phi*S_g*HI_g)_i*[1 - exp(-W_j/T_{1g})] j = 1, 2, 3 \qquad (14)$$

I-11. By standard mathematical techniques, one can solve for the three unknowns at each $T_{2i}$ value: $(\phi*S_w*HI_w)_i$, $(\phi*S_o*HI_o)_i$, and $(\phi*S_g*HI_g)_i$. Go to step 13.

I-12. [From Step 7] Find the difference $$P(T_{2i}, W_2) - P(T_{2i}, W_1) = (\phi*S_g*HI_g)_i*[exp(-W_1/T_{1g}) - exp(-W_2/T_{1g})] \qquad (15)$$

I-13. To find the total gas signal, sum $(\phi*S_g*HI_g)_i$ over all $T_{2i}$.

I-15. To find the gas saturation, $S_g$, the quantities $\phi$ and $HI_g$ are determined as explained below.

Method II Flow Chart

Figure 3:
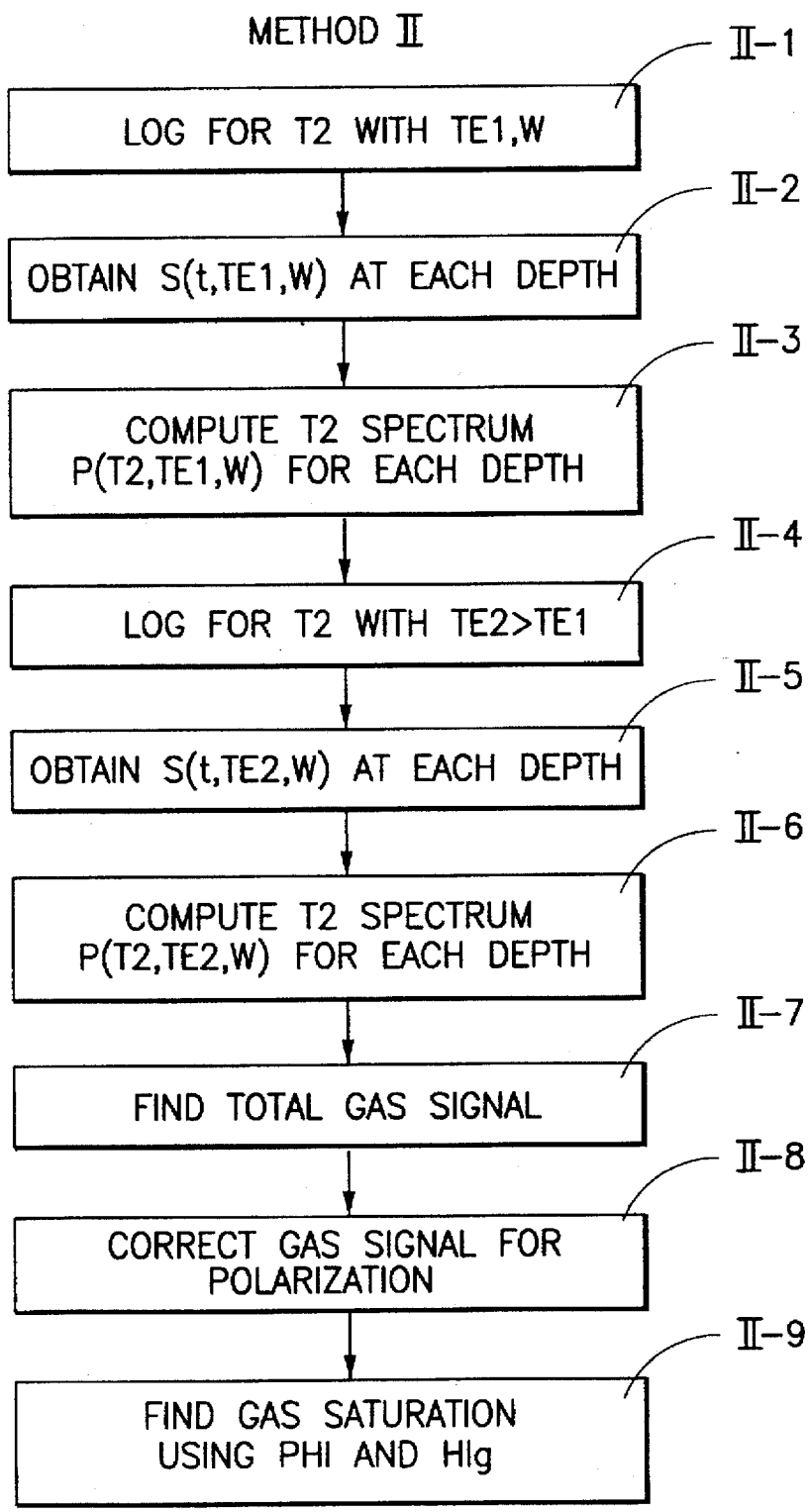

FIG. 3 illustrates this method.

II-1. Log the formation for $T_2$ using echo spacing $T_E^1$ and wait time W. W should be at least comparable to the expected $T_1$ of the gas; 3 sec for example.

II-2. Obtain the signal $S(t, T_E^1, W)$ at each depth.

II-3. Compute the $T_2$ spectrum $P(T_2, T_E^1, W)$ for each depth.

II-4. Log the formation using echo spacing $T_E^2$ which is longer than $T_E^1$.

II-5. Obtain the signal $S(t, T_E^2, W)$ at each depth.

II-6. Compute the $T_2$ spectrum $P(T_2, T_E^2, W)$ for each depth.

Note that it is possible to acquire logs for $T_E^1$ and $T_E^2$ in an interleaved manner, so that only a single logging pass is required.

II-7. Use one of the methods given below to determine the gas signal, $(\phi*S_g*HI_g)(W)$, a function of the wait time.

II-8. Correct the gas signal for polarization effects:

$$\phi S_g HI_g = \phi S_g HI_g(W)/[1 - exp(-W/T_{1g})] \qquad (16)$$

II-9. To find the gas saturation, $S_g$, the quantities $\phi$ and $HI_g$ are determined as explained below.

Signal Processing for Method II

In Method II, increasing the echo spacing causes the gas contribution to shift to shorter $T_2$. There are two ways to quantify the gas signal.

In the first method, the $T_2$ spectra are differenced: $P_{diff}(T_2)=P(T_2,T_E^1)-P(T_2,T_E^2)$. Components that do not move (e.g. water in small pores) are not present in the difference spectrum, and the gas signal in the $T_E^1$ spectrum is inverted. Then the quantity of gas is found by summing the absolute value of the difference spectrum:

$$(\phi^*S_g^*HI_g) = \frac{1}{2} \sum_i |P_{diff}(T_{2i})| \quad (18)$$

This method is reliable when the gas signals in the two spectra do not overlap.

A more reliable method is to use a matched filter technique. When Method II is in use (large pores) internal gradients are unimportant. Thus, for a given tool and echo spacing, the gas component of the spectrum can be predicted; only the amplitude is unknown. Using well-known matched filter techniques, the quantity of gas can in principle be determined from a single spectrum. The use of two or more spectra collected with different $T_E$ values makes the estimation much more reliable.

Method III Flow Chart

Figure 4:
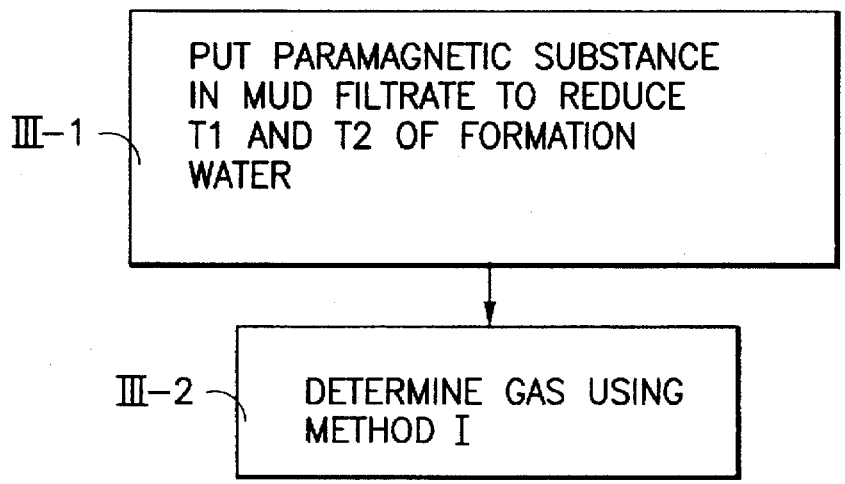

FIG. 4 illustrates this method.

III-1. Introduce a paramagnetic substance such as Mn-EDTA into the mud filtrate to reduce $T_1$ and $T_2$ of the formation water.

III-2. Determine gas using Method I.

Method IV

Gas Detection: Low Pressure Gas

Methods I, II, and III work when there is a detectable NMR signal from gas. The NMR signal is directly proportional to the hydrogen index. When gas zones are at low pressure (e.g. either shallow or an air-drilled hole) the hydrogen index is low. In such circumstances, NMR tools measure only the liquid-filled porosity, which is less than the porosity measured by lithodensity, sonic, or other logs. The gas volume is then the difference between lithodensity porosity and NMR porosity.

As an example of low pressure gas detection, consider a formation with a porosity $\phi=0.2$ and a gas saturation $S_g=0.25$. If for a particular NMR logging tool $\phi^*S_g^*HI_g=0.02$ can be detected, then in order to use Methods I, II or III it is necessary that $HI_g>0.4$. This corresponds to a gas pressure of 4000 psi and a temperature of 150 F. [Schlumberger Log Interpretation Principles/Applications (1987) pg 45]. If $HI_g<0.4$, then gas volume is best detected by comparing NMR porosity to lithodensity, sonic, or other porosity logs.

Determination of Hydrogen Index and Porosity

1. The hydrogen index of water is determined primarily by its salinity. NMR well logging tools have a shallow depth of investigation, so the water is predominantly mud filtrate, the composition of which is well known to the logging engineer. $HI_w\sim1$ in most cases.

2. The hydrogen index of the oil and the gas are determined by their composition, temperature and pressure. Typically, the compositions of gas and oil in a given geological formation are known from previous production experience. The temperature can be estimated from a linear interpolation between surface and bottom hole temperatures, or can be easily measured with a downhole thermometer. The pressure is accurately estimated from the density of the borehole fluid ("mud"), which is known to the logging engineer, and the true vertical depth of the formation of interest, which is known. $HI_o\sim1.0$ in many cases. $HI_g$ is usually in the range 0.1 to 0.7.

3. $(\phi^*S_w^*HI_w)$, $(\phi^*S_o^*HI_o)$, and $(\phi^*S_g^*HI_g)$ can be found by means described above. The porosity is equal to $$\phi=(\phi^*S_w^*HI_w)/HI_w+(\phi^*S_o^*HI_o)/HI_o+(\phi^*S_g^*HI_g)/HI_g \quad (17)$$

Gas Effect in NMR: Reduced $T_2$ Relaxation Times Due to Diffusion

The diffusion coefficient of gas under reservoir conditions can be more than ten times larger than that of water, making the $T_2$ relaxation time of gas more sensitive to static magnetic field gradients. In formations where gas occupies pores larger than about 10 μm, this $T_2$ effect (effect of diffusion on the measured $T_2$ relaxation times of gas) can be used to identify gas even though the tool gradients are not uniform.

Three contributions to the $T_2$ relaxation rate are:

$$1/T_2=(1/T_2)b+(1/T_2)s+(1/T_2)d \quad (2)$$

where the subscripts s, b and d stand for surface, bulk and diffusion, respectively. The first two contributions are discussed above. The third contribution in Eq. (2) is due to diffusion in magnetic field gradients. Diffusion of the spins in an inhomogeneous magnetic field leads to a dephasing which cannot be refocused by 180° pulses. For the CPMG sequence, the resulting relaxation rate for unrestricted diffusion is known as:

$$\left.\frac{1}{T_2}\right|_{d,unrest} = \frac{1}{12} D\gamma^2 g^2 T_E^2, \quad (19)$$

where $\gamma=2\pi\times4258_s^{-1}G^{-1}$ is the gyromagnetic ratio, g is the strength of the magnetic field gradient and $T_E$ is the echo spacing. In general, a very short echo spacing $T_E$ is used such that $1/T_{2,d}<<1/T_{2,s}$ for water. Since for a gas the diffusion coefficient D is much larger and $1/T_{2,s}$ is much smaller than for water, the relaxation rate $1/T_2$ for gas can be dominated by the diffusion contribution $1/T_{2,d}$. In turn, by varying $T_E$, the size of the diffusion term can be deliberately increased and used for gas detection.

In contrast to $T_2$ relaxation, there is no diffusion term for $T_1$ relaxation, discussed above:

$$1/T_1=(1/T_1)b+(1/T_1)s \quad (1)$$

For gas (or oil in water wet rocks), the surface term is again negligible compared to the bulk term, so that we expect $T_1(gas)\cong T_{1,b}(gas)$. For methane at typical reservoir conditions, this is about 4s. In contrast, typical $T_1$ values for water are much shorter, because the surface term in Eq. (1) dominates in this case. Only in rocks with vuggy porosity, where the ratio of surface area to volume is very small, one can observe $T_1$ values of water that are as long as those of gas.

The inventors have focused on the diffusion term $1/T_{2,d}$ in Eq. (2) and estimate the size of this effect quantitatively for the CMR. To do this, literature values for the diffusion coefficients at the relevant reservoir conditions and the strength of gradients are needed (both discussed below). The expression given for the diffusion term in Eq. (19) only applies as long as restrictions in the pore space can be neglected. In "Diffusion Enhanced T2 Relaxation Rate", the conditions are given for this approximation to hold true. In many rocks, the conditions for unrestricted diffusion do not hold. The effect of diffusion on the decay rate depends then on the microgeometry of the rock and the fluid distribution. Three different cases are considered and it is shown that the diffusion effect becomes much smaller in all of them.

Published Diffusion Coefficients

Figure 5:
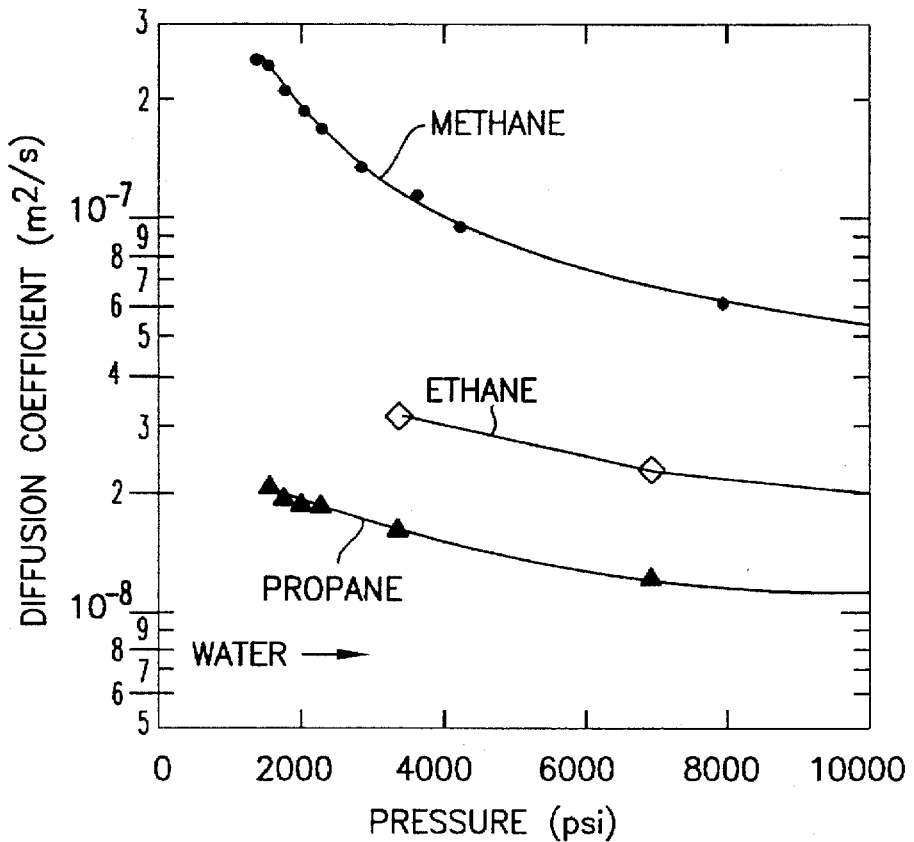
FIG. 5 illustrates diffusion coefficients for Methane, Ethane, and Propane at 190° F.

The diffusion coefficient D of a gas is in general much larger than for a liquid, such as water or oil. At reservoir conditions, the gas is above the critical point and called a fluid. The diffusion coefficient depends on the fluid composition, the temperature and the pressure. Diffusion coefficients are available from the published literature. Therefore, it is not necessary to measure the diffusion coefficient of the fluid in a reservoir with an NMR tool. In FIG. 5, literature diffusion coefficient values for pure methane, ethane and propane are shown versus pressure for T≅190° F. Published experimental diffusion coefficient values for mixtures of methane and propane lie between the curves of the pure fluids. It has been shown that there is only a weak pressure dependence for water, and its diffusion coefficient at T=190° F. is $7.7 \times 10^{-9}$ m$^2$/s. This implies that at typical reservoir conditions, the diffusion coefficient of methane can be more than 10 times as large as for water; however, the contrast between propane and water is only about a factor of 2.

Magnetic Field Gradient

The magnetic field gradients that are experienced by spins in the pore space of a rock have two contributions: (i) tool gradients and (ii) rock internal gradients induced by the susceptibility contrast between rock and pore fluid. The tool gradients are a property of the magnet design of each tool. The CMR was designed so that the magnetic field at the center of the sensitive zone is as uniform as possible. The sensitive region is formed around a saddle point of the magnetic field profile and can be approximated by:

$$B(x,y) \approx B_0 + 20 \frac{G}{cm^2} (y^2 - x^2) \qquad (20)$$

The local field inhomogeneities therefore vary across the sensitive region. To first order, this can be analyzed as a distribution of gradients, the curvature of the field profile is not important. Even with a high diffusion coefficient, each spin explores only a small region of this field profile in the measurement time. During the life time $T_2(\leq 4s)$, the spins diffuse at most a distance of the order of $\sqrt{DT_2}$, which is always less than 1 mm. Therefore, we can neglect the curvature of the field and use a distribution of gradients.

With the field distribution given in Eq.(20), the magnitude of the local gradient g is only a function of the distance $r \equiv \sqrt{x^2 + y^2}$ $$g = 40 \frac{G}{cm^2} r. \qquad (21)$$

Figure 6A:
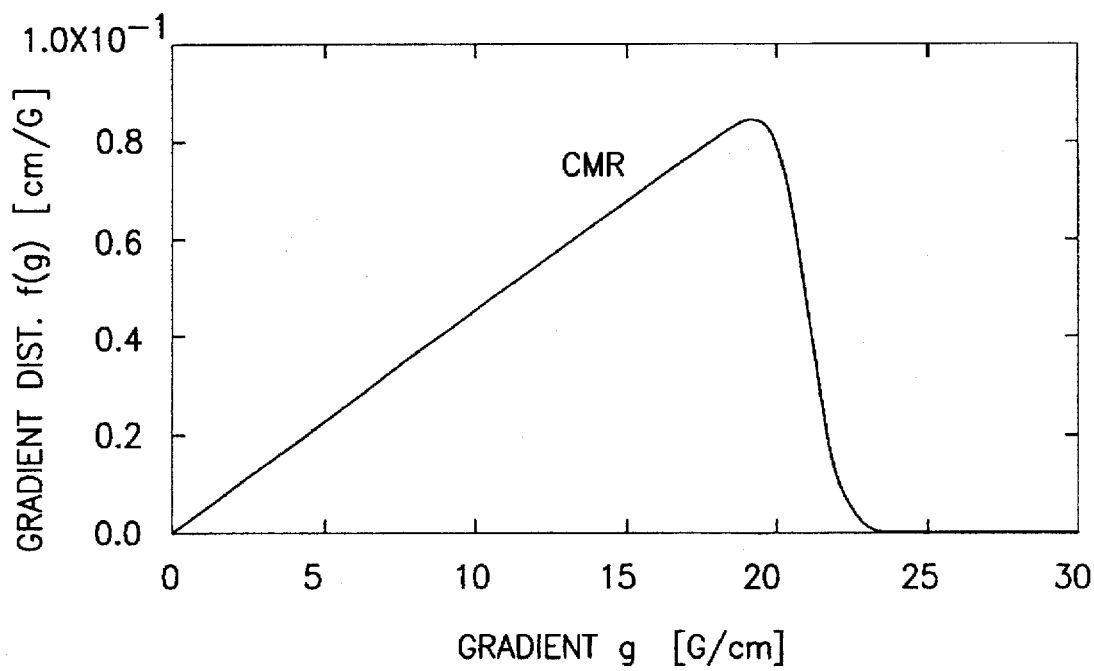
FIGS. 6a and 6b respectively illustrate the distribution function of tool gradients and the square of the gradient.
Figure 6B:
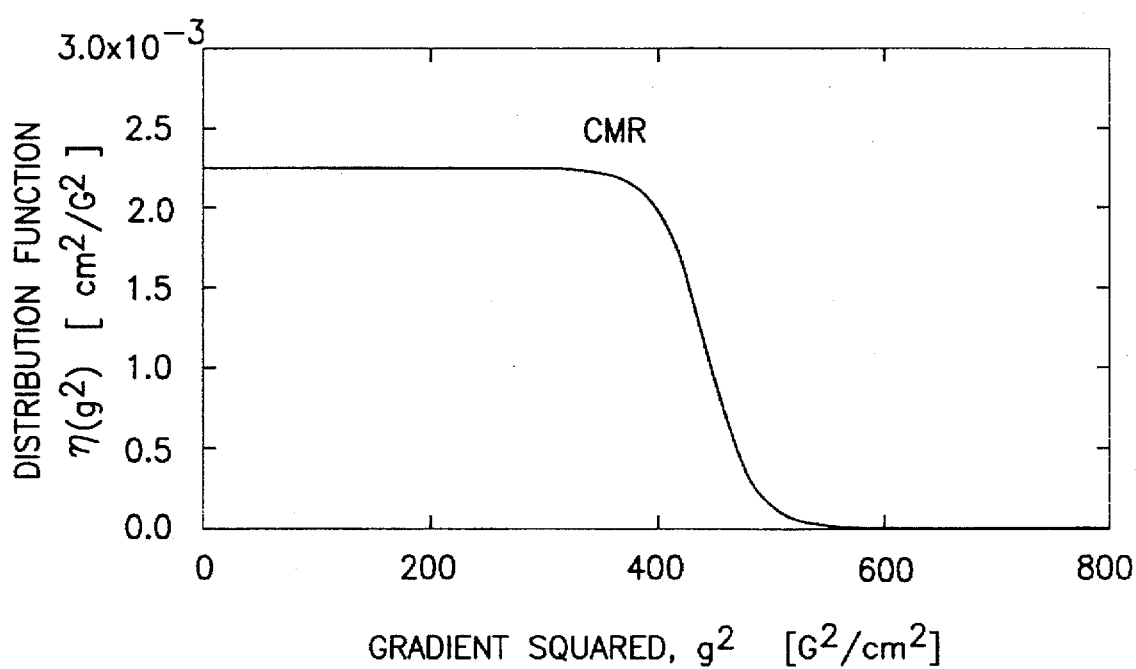

The radial extent of the sensitive region is mainly determined by the magnitude of the rf pulse $B_1$. With $B_1 \approx 5G$ we obtain $r_{max} \approx \sqrt{B_1/20 G cm^{-2}} \approx 0.5$ cm This leads to a distribution of gradients between 0 and about 20 G/cm This is schematically illustrated in FIGS. 6a and 6b. We have both plotted the distribution function of the gradient, f(g), and the distribution function of the square of the gradient, η(g$^2$). Internal gradients are induced by the susceptibility contrast $\Delta_\chi$ between the rock grains and the pore fluids. The magnetic susceptibility of the rock can vary significantly from rock to rock. The gradient strength depends also on the microgeometry, but as a rough estimate, we expect it to be inversely proportional to pore size:

$$g_{int} \approx \alpha \frac{\Delta_\chi B_0}{l_p}, \qquad (22)$$

where α is a geometrical parameter of order unity, $B_o$ is the static field and $l_p$ is the pore size. Using α=0.5, $\Delta_\chi$=10−4 and Bo=450 Gauss, we obtain for an order of magnitude estimate $$g_{int} \approx (22.5 \ G/cm)(10 \ \mu m/l_p), \qquad (23)$$

This shows that internal gradients in smaller pores can be at least as strong as the tool gradients. The tool gradients are therefore only the lower limit of the total gradients in the rocks.

Diffusion Enhanced $T_2$ Relaxation Rate

As was mentioned in the introduction, diffusion of the spins in a magnetic field gradient leads to enhanced $T_2$ relaxation. The size of the effect depends on the gradient strength and the pore size, because the rock grains restrict the diffusing spins. In large pores, the presence of the pore walls can be ignored to first order and the theory of unrestricted diffusion can be applied. In rocks with small pores, the diffusion of spins is strongly affected by the pore walls and a theory of restricted diffusion has to be used. There is a critical length $l_g$ that controls the importance of restricted diffusion. It is defined by:

$$l_g \equiv \left( \frac{D}{\gamma g} \right)^{1/3} \qquad (24)$$

Figure 7:
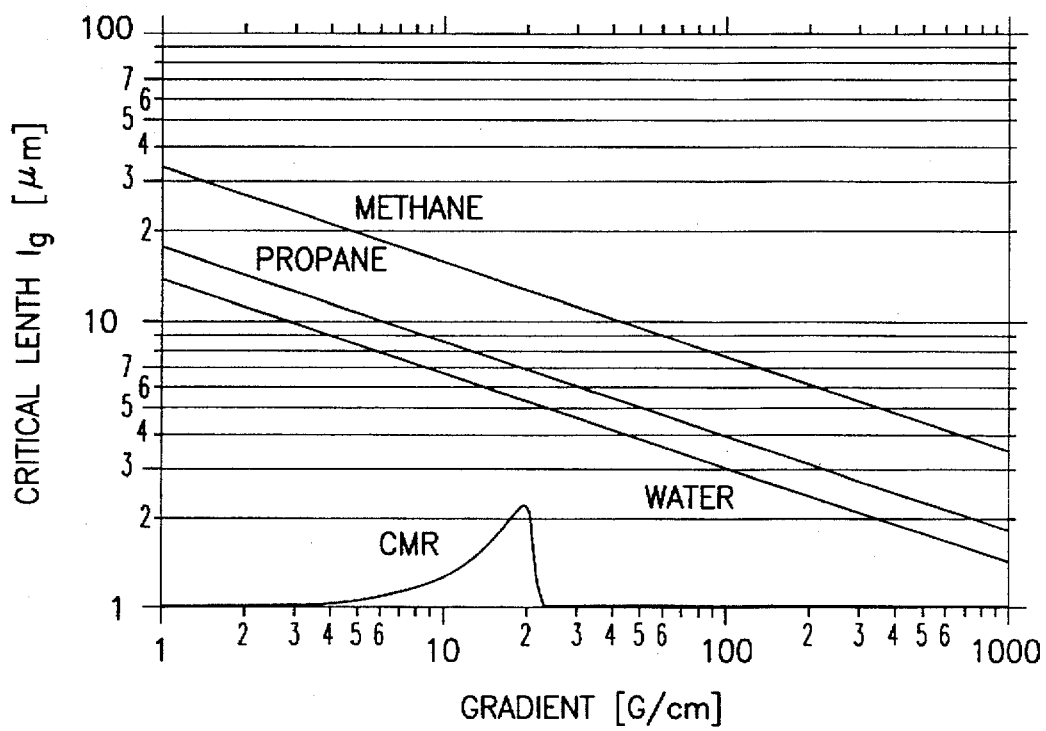
FIG. 7 shows critical length plotted as a function of gradient strength for different fluids.

It can be thought of as the distance over which a spin has to diffuse to dephase by 2π. If the pores in a rock are larger than $l_g$, unrestricted diffusion (see Eq. 19) will adequately describe the effect of the gradients. In FIG. 7, the critical length $l_g$ is plotted versus gradient strength for different fluids, using diffusion coefficients at 4000 psi and 170° F. as shown in FIG. 5. Also shown are the strengths of the tool gradients. We conclude that the critical length $l_g$ is of the order of a few microns to a few tens of microns.

Large Pores: Unrestricted Diffusion

Figure 8A:
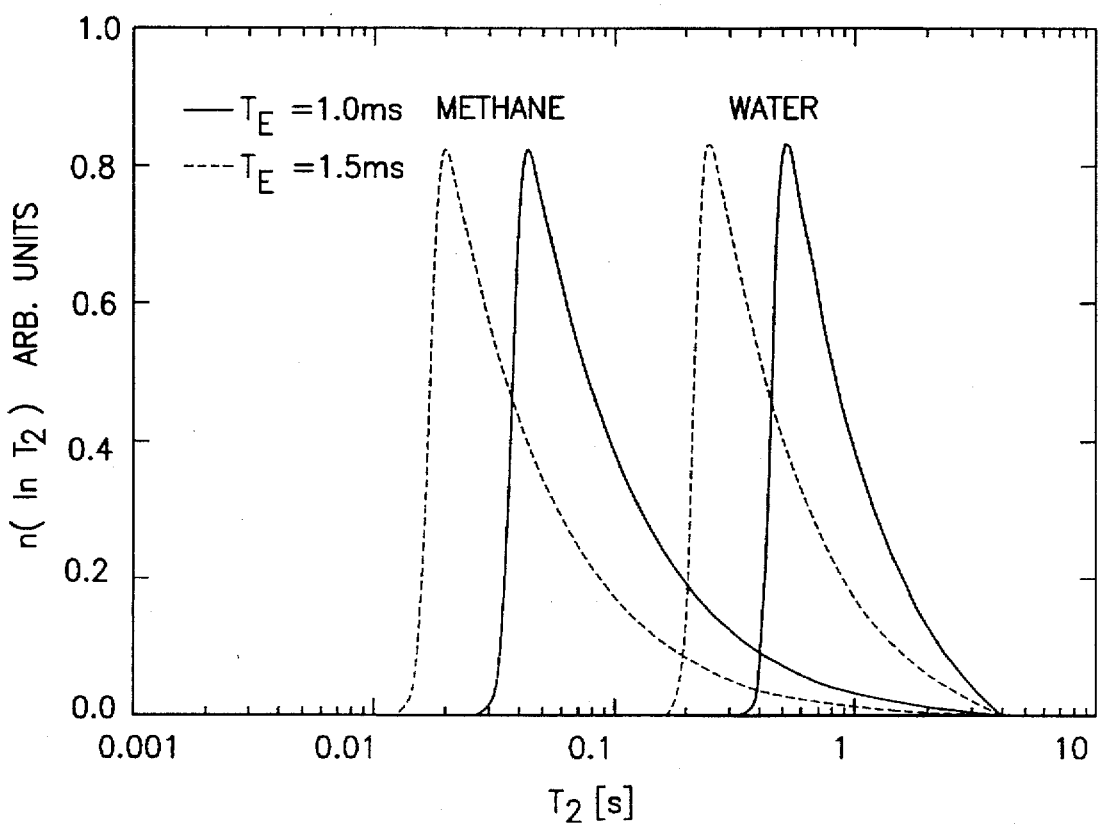
FIGS. 8a and 8b respectively illustrate, for two different echo spacings $T_E$, T2 distributions from free diffusion of gas and water in large pores; and gas in large pores and water in small pores.

From FIG. 7, we can see that in pores larger than about 10 μm, the diffusion enhanced relaxation can be described by the theory of unrestricted diffusion. In this regime, the restrictions are not important because the spins dephase before they have encountered the pore walls. Eq. (19) can then be applied for the diffusion contribution. In FIG. 8a, the resulting $T_2$ distributions for methane and water are presented, using two different echo spacings $T_E$. The two different values for $T_E$ are 1 ms and 1.5 ms. In this graph, a bulk $T_2$ of 4s has been assumed in both cases and surface relaxivity has been ignored. It is evident from FIG. 8a that the relaxation time of methane can be significantly shortened by the diffusion effect. It is rather sensitive to the experimental value of echo spacing, $T_E$. This is a parameter that can be controlled in the downhole NMR tools. In the absence of internal gradients, the $T_2$ distribution of methane measured with other NMR tools would be sharp, whereas there is a wider distribution for the CMR. In the CMR, some spins are in a region of small gradients and not affected by diffusion in the gradient. This leads to the long tail on the right hand side of the distributions.

For methane, the distributions shown in FIG. 8a are expected to be the observed $T_2$ distribution, because the surface term should be negligible. In the case of water, this $T_2$ distribution is only measured for water in large vuggy pores, where surface relaxation can be neglected. When the effect of surface relaxation is considered, the relaxation rates of water are also affected by diffusion, but by a smaller degree than gas.

Figure 8B:
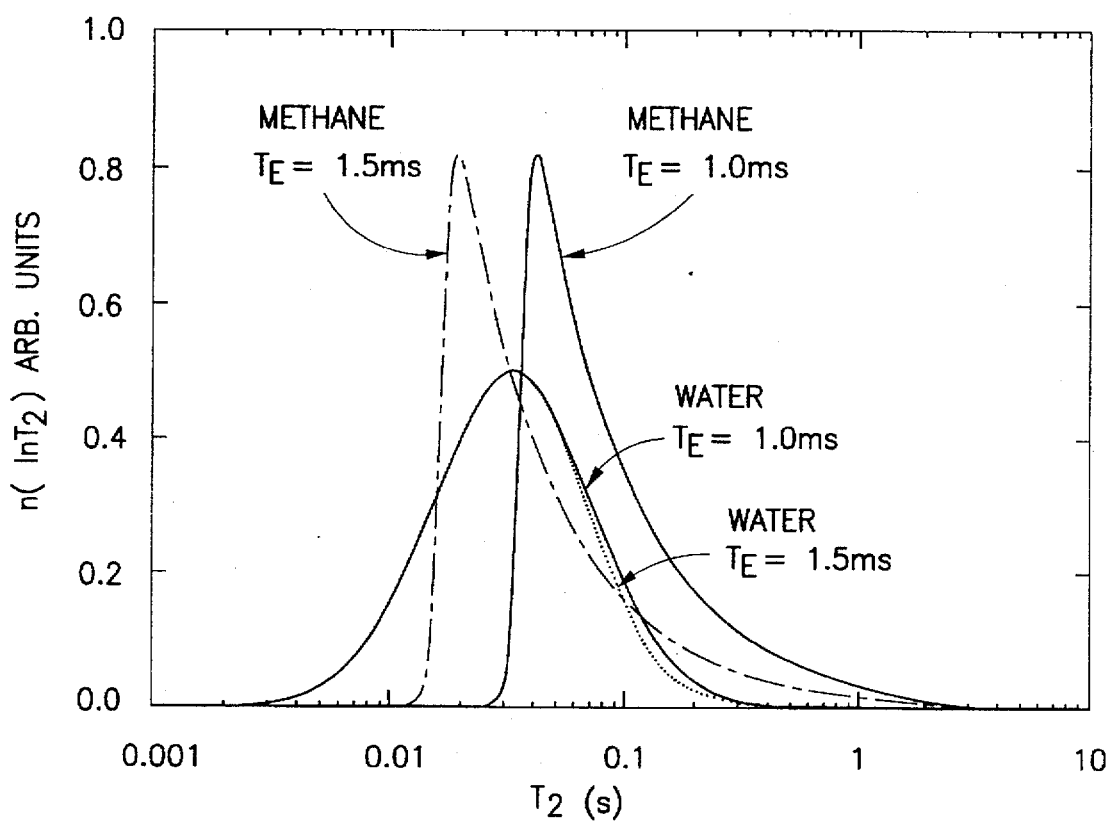

In another important case, gas occupies the large pores, but water lines the large pores and fills the smaller pores. The relaxation time of water is then affected by surface relaxation. As an illustration, we plot in FIG. 8b the resulting $T_2$ distributions, assuming a typical $T_2$ distribution due to surface relaxation for water. We chose it such that there is a significant overlap between the water and gas $T_2$ distributions. FIG. 8b shows clearly that the two contributions can be separated by varying the echo spacing $T_E$. The two different values for $T_E$ are 1 ms and 1.5 ms. The relaxation times of gas are much more affected than water by a modest change in $T_E$.

The results of FIGS. 8a and 8b for unrestricted gas diffusion could be changed by the presence of large internal gradients. However, in the majority of rocks with large pores, it is not expected that internal gradients would be much larger than the tool gradients.

Small Pores: Restricted Diffusion

For pores smaller than $l_g$, restrictions in the pore space become important and the reduction in relaxation times due to diffusion is smaller. The magnitude of this effect depends on the exact geometrical arrangement of the fluid. For the general case, we can only give some asymptotic results to illustrate the range of possible responses. The diffusion effect in the tool gradients depends on the way the pores are connected, or more precisely, how the fluids in different pores are connected. In one extreme, the gas is confined in a pore and is not connected through the throats to the gas in the next pore. This is a very plausible scenario in rocks with narrow throats, where the throats are filled with liquid by capillary action. At these threshold saturations of 10 to 20%, the pore throats are blocked by liquid water. For our calculation, we make the further assumption that the shape of the gas in the pores can be approximated by spheres. The relaxation rate in small pores of size $l_p$ is then given by:

$$\frac{1}{T_2}\bigg|_{d,rest} = \frac{8}{175} \frac{\gamma^2 g^2 l_p^4}{D} . \quad (25)$$

This expression is correct in the limit that the pore is small compared to $l_g$ and that the spins can traverse the pore many times between the 180° pulses, i.e., $l_p < \sqrt{DT_E}$. For methane and $T_E = 0.5$ ms, this corresponds to $l_p < 7$ μm. Note that Eq. (25) does not depend on $T_E$, i.e., varying the echo spacing cannot be used to distinguish $1/T_{2,d}$ from the other contributions in this case.

To interpolate between the diffusion effect in large pores (Eq. 19) and in small pores (Eq. 25), the simplest interpolation has been used to get an estimate over the whole range:

$$(T_2)_d = (T_2)_{d,unrest} + (T_2)_{d,rest}. \quad (26)$$

Figure 9A:
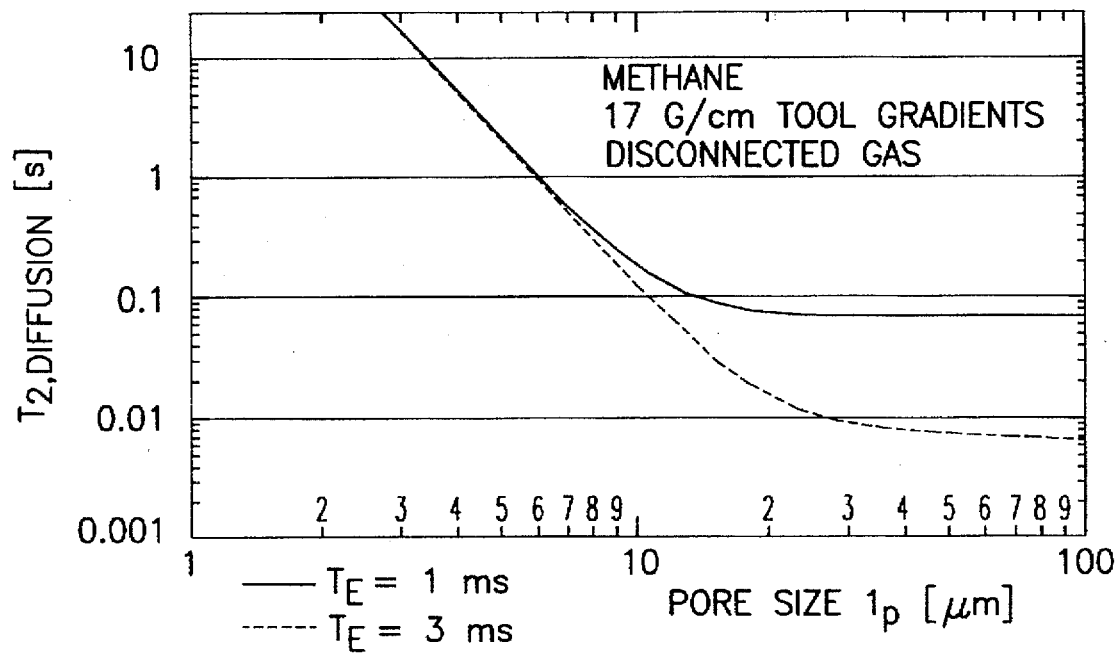
FIG. 9a illustrates resulting diffusion enhanced relaxation time T2 as a function of pore size for two different echo spacings $T_E$.

In FIG. 9a, the resulting diffusion enhanced relaxation time $(T_2)_d$ for methane in a tool gradient of 17 G/cm is plotted versus the pore size for two different pulse spacings $T_E$. It is assumed that the gas bubbles in different pores are disconnected. No internal gradients are indicated.

Figure 9B:
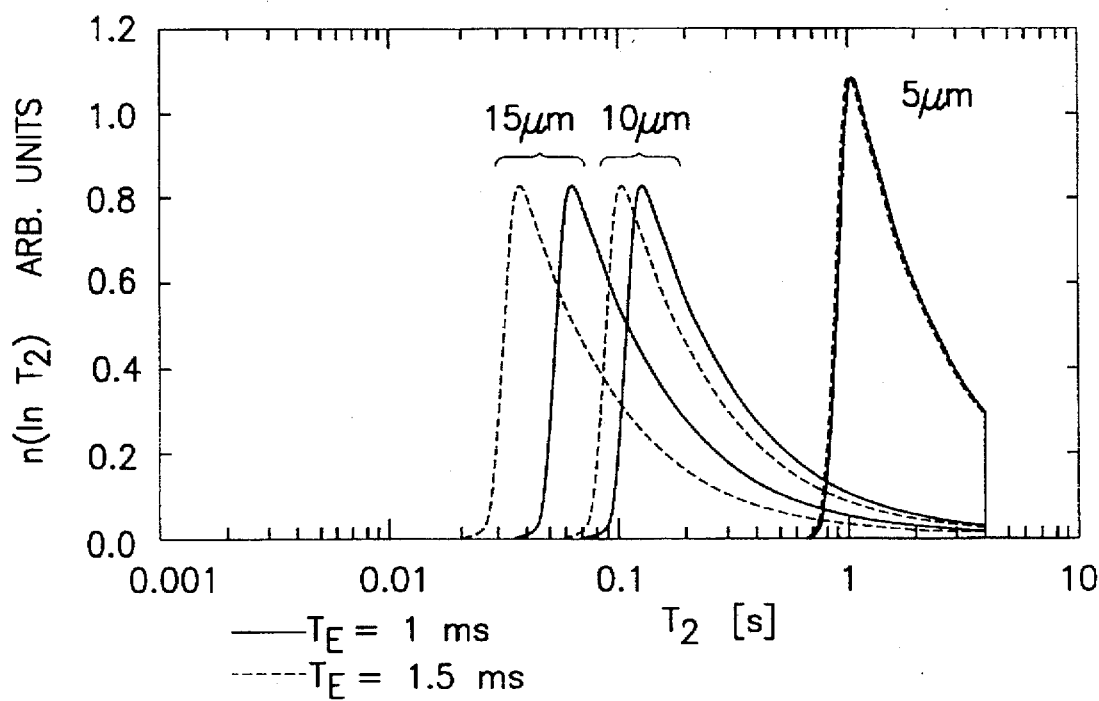
FIG. 9b illustrates calculated T2 distributions for Methane for two different echo spacings $T_E$.

In the case of the CMR, the distribution of gradients leads to a distribution of $(T_2)_d$, analogous to those shown in FIGS. 8a and 8b, with a peak in the distribution that is close to that shown in FIG. 9a. Notice that for pores smaller than about 4 μm, $(T_2)_d > (T_2)_b \cong 4s$ and the diffusion effect for gas is then negligible. This is further illustrated in FIG. 9b, which plots the calculated $T_2$ distributions for methane in the CMR tool gradient, assuming that the gas is confined in pores of size 5 μm, 10 μm and 15 μm, respectively. This plot includes the bulk relaxation time of methane (4s). No internal gradients are indicated.

Consider the other extreme limit of restricted diffusion, where the fluid is well connected between pores. Eq. (25) then underestimates the diffusion enhanced relaxation rate. In small pores, the diffusion of spins can then be characterized by a diffusion coefficient that is reduced by the tortuosity. In this case, Eq. (19) is applied but with the reduced diffusion coefficient $D_\infty = D/F\phi$ where F is the formation factor and $\phi$ is the porosity. Assuming that the Archie exponent m=2, $D_\infty = \phi D$ is obtained. To estimate the resulting relaxation times for rocks with small, well connected pores, simply multiply the relaxation times in Eq. (1) by $\phi^{-1}$, i.e. a number typically in the range of 3–10.

$$T_2|_{d,conn} = \frac{12}{D\phi \gamma^2 g^2 T_E^2} , \quad (27)$$

Figure 10:
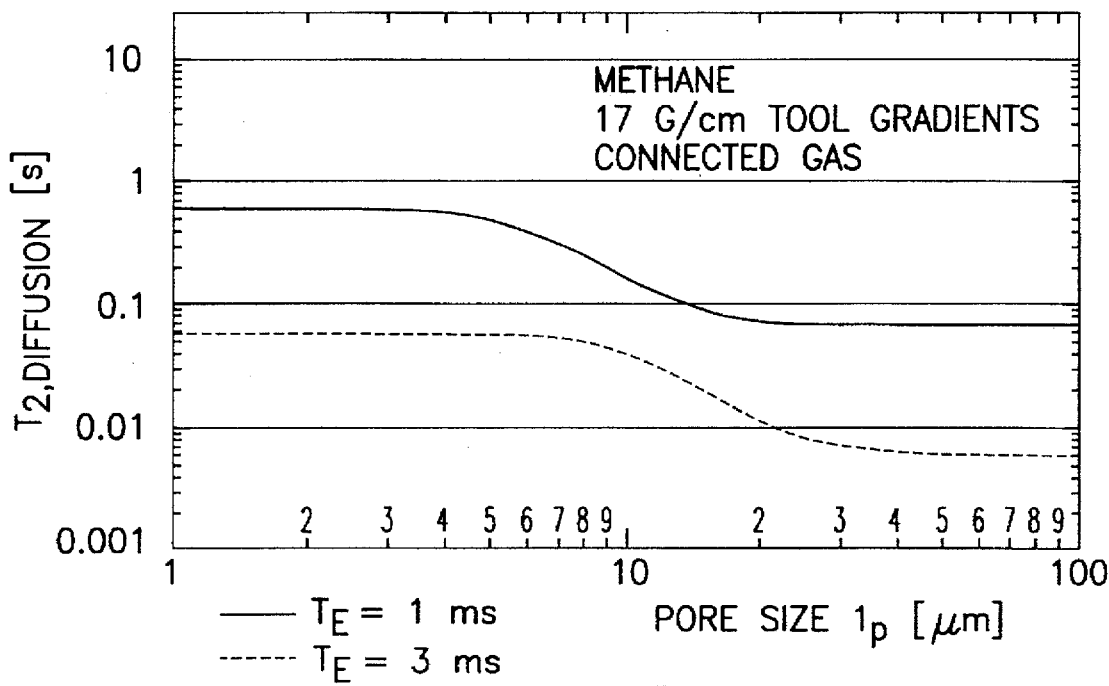
FIG. 10 illustrates T2 relaxation time of Methane due to diffusion for two different echo spacings $T_E$ without internal gradients.

The resulting $T_2$ relaxation time due to diffusion in gas filled pores where the gas is well connected is shown in FIG. 10 for $\phi=10\%$. Again simple interpolation is used between large and small pores. FIG. 6 illustrates T2 relaxation time of Methane due to diffusion for two different echo spacings $T_E$. The two different values for $T_E$ are 1 ms and 1.5 ms. No internal gradients are indicated. In small pores, where relaxation times in FIG. 10 are shorter than in FIG. 9a, but still longer than in large pores, where the restrictions in the pore space are not important.

Figure 11:
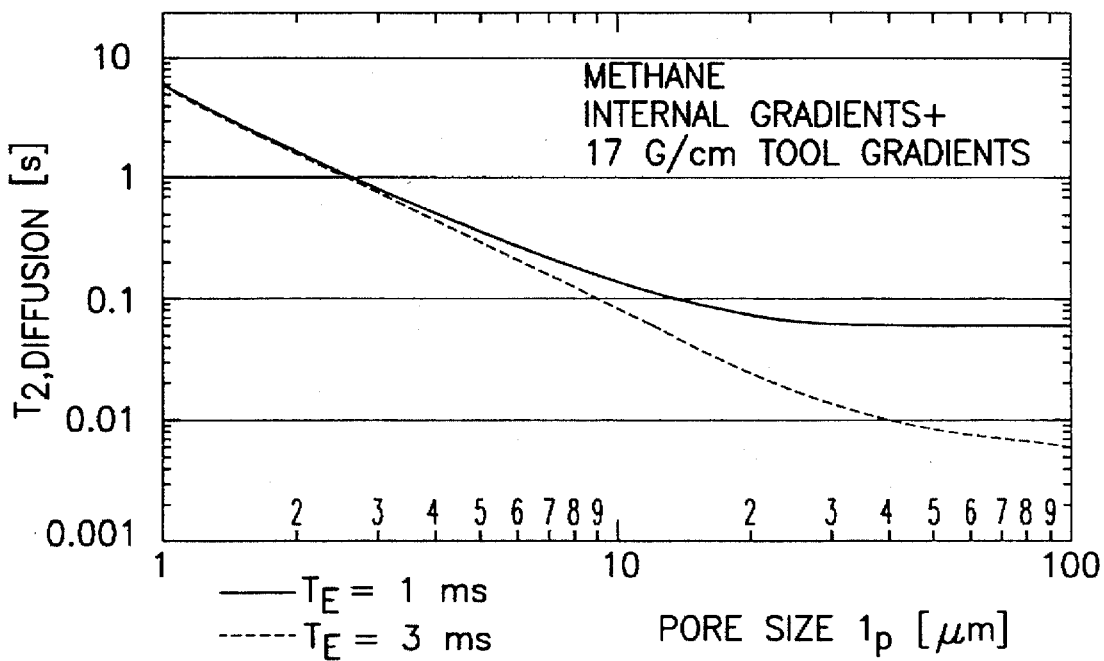
FIG. 11 illustrates T2 relaxation time of Methane due to diffusion for two different echo spacings $T_E$ with internal and tool gradients.

Finely, consider the effects of internal gradients. As discussed before, internal gradients might dominate tool gradients in small pores. To lowest order, internal gradients are quasi-periodic, in which case Eq. (25) applies in small pores, independent of the connectivity of the gas in the pores. Using the parameters for the internal gradients given in Eq. (23), the values shown in FIG. 11 are obtained. FIG. 7 illustrates the effect in small pores of internal and tool gradients. FIG. 7 shows T2 relaxation time of Methane due to diffusion for two different echo spacings $T_E$ with internal and tool gradients. The two different values for $T_E$ are 1 ms and 1.5 ms. In small pores, the relaxation time increases slower ($\propto l_p^{-2}$) than in the case of disconnected gas in the tool gradient shown in FIG. 9a ($\propto l_p^{-4}$). However, in both cases, gas in small pores is not efficiently dephased by diffusion anymore.

To summarize, gas under downhole conditions can have a significantly reduced $T_2$ relaxation time when measured with the CMR tool. This effect is most pronounced in rocks with pores larger than about 10 μm. The wide distribution of gradients results in a distribution of relaxation times for gas as shown in FIGS. 8a and 8b. For other NMR tools, having a tool gradient which is approximately uniform, the distribution of relaxation times is expected to be narrower. In the larger pores, the diffusion effect is the dominant $T_2$ term for gas and can be separated from water and oil signals by changing the echo spacing $T_E$, which is a tool parameter.

Pulse Sequences, Varied Spacing Between Pulses

Figure 12A:
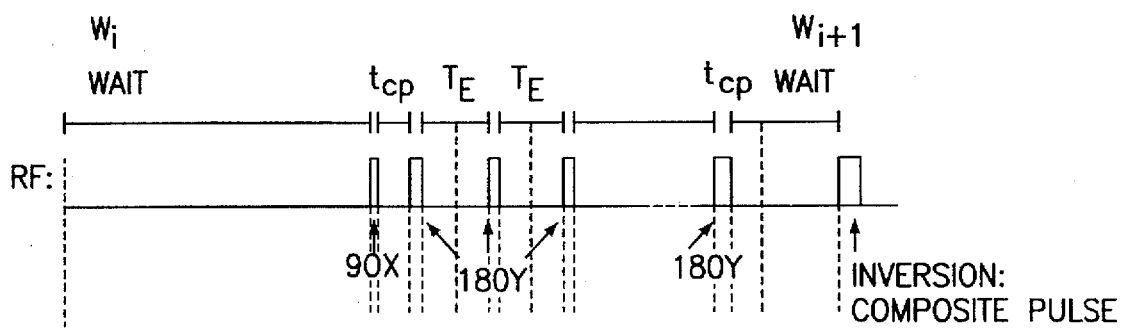
FIGS. 12a–e, are graphs over time respectively of the pulse sequence of the invention, and the resulting longitudinal magnetization and measurable signal.
Figure 12B:
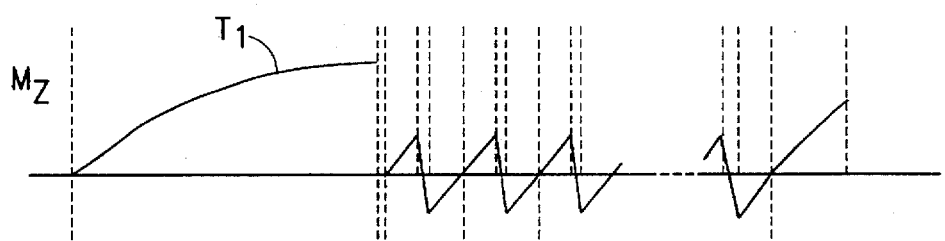
Figure 12C:
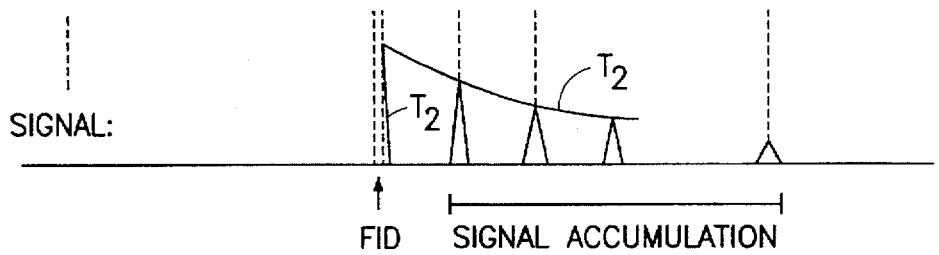
Figure 12D:
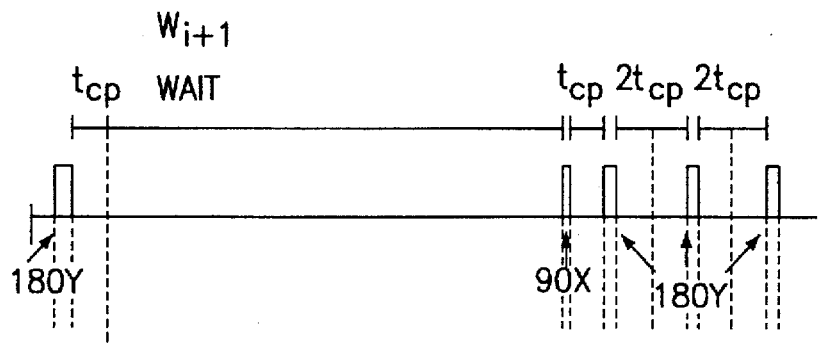
Figure 12E:
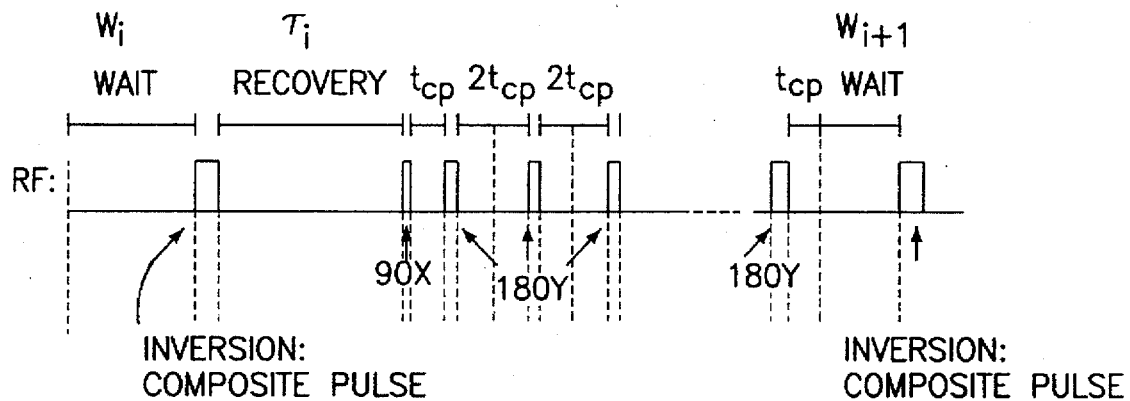

Turning to FIGS. 12a–e, the preferred pulse sequence conducted by the borehole tool of U.S. Pat. Nos. 4,933,638, 5,055,787, and 5,055,788, is seen in graphic form. At the start of any (e.g., i'th) sequence after waiting for a waiting period $W_i$, the spin system is at zero transverse magnetization (as seen in FIG. 12c) and at a positive longitudinal magnetization which is less than the full equilibrium magnetization (as seen in FIG. 12b). During the so-called waiting time $W_i$ the nuclear magnetization of the formation under investigation begins to relax towards the direction dictated by the static field. The rate at which a nuclear spin returns toward the static field is governed by the spin lattice relaxation time (T1) which is of great interest. A ninety degree pulse is applied to the formation, causing the spins which have relaxed somewhat (according to the decay T1) to tip into the measurement plane where they generate a free induction decay (FID) signal in the measurement coil of the borehole tool. Because the deadtime of the borehole tool is on the order of fifty microseconds which is longer than the free induction decay time, the FID is not observed. However, by using the ninety degree pulse as the first pulse in a Carr-Purcell-Meiboom-Gill sequence, and as will be explained shortly, indications of T1 and T2 are obtained.

At a time $t_{cp}$ (Carr-Purcell time) after the ninety degree pulse, a one hundred eighty degree pulse is applied, and as seen in FIG. 12a, further one hundred and eighty degree pulses (known as refocussing pulses) are applied every $T_E$ or $2t_{cp}$, in accord with the CPMG sequence. These one hundred eighty degree pulses generate measurable echoes at times $t_{cp}$ after each refocussing pulse. As indicated in FIG. 12c, the magnitude of the echoes decays over a period of time. The rate of decay is dictated by the spin-spin or T2 relaxation parameter. By applying many one hundred eighty degree pulses, numerous echo points are available for providing a decay curve indicative of T2. These numerous echoes permit a more accurate determination of the T1 relaxation parameter which is not obtainable otherwise.

According to the invention, it is sufficient to vary any one timing parameter of individual sequences to see the gas attribute, or gas effect. For example, it is sufficient that $W_i$ of the first sequence is different from $W_{i+1}$ of the second sequence. See FIG. 12e. Or, $T_{Ei}$, $t_{cpi}$ or $\tau_i$ of the first sequence is different from the $T_{Ei+1}$, $t_{cpi+1}$ or $\tau_{i+1}$ of the second sequence. Generally, $T_E=2t_{cp}$. Varying W, $T_E$, $t_{cp}$, or $\tau$ changes the timing pattern of subsequent pulse sequences. Thus, varying any one timing parameter W, $T_E$, $t_{cp}$, $\tau$ provides a first pulse sequence having a first timing pattern (see FIG. 12a) and then a second pulse sequence having a different, second timing pattern. Subsequent pulse sequences may have other different timing patterns or repeats of prior timing patterns.

Figure 13:
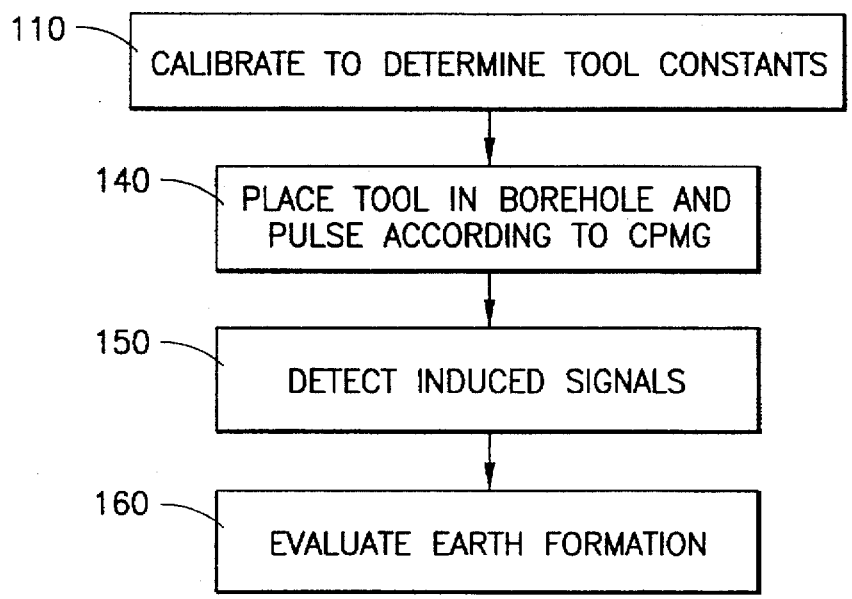
FIG. 13 is a flow chart in block diagram indicating steps to determine a gas attribute of a formation.

Such a sequence has two main advantages over inversion recovery methods of measuring T1. First, the proposed method does not depend on a measurement of a free induction decay which is lost in the instrumental deadtime of a borehole tool. Second, the amplitude information needed for the T1 determination consists of a multiplicity of echoes following each wait—recovery segment instead of one FID determination. Since the waiting and recovery times are very time consuming, it is clearly advantageous to collect as much amplitude information as possible on each wait—recovery cycle Turning to FIG. 13, a flow chart of the practice of the preferred embodiment of the invention, and results obtained in a laboratory test are provided. Prior to the use of the tool for investigating rock samples, the tool disclosed in U.S. Pat. Nos. 4,933,638; 5,055,787 and 5,055,788 and was calibrated at 110 by performing a CPMG measurement on a NiCl doped water sample to determine the tool constants a and c. The CPMG pulse sequence with phase alternation was conducted by the apparatus and the spin echoes were recorded at 150. The formation is then evaluated in light of signals which have been induced in the formation and which have been received by the tool at 160.

It will be appreciated that in the borehole, continuous logs of porosity, permeability, irreducible water saturation, etc., can be derived from the NMR tool measurements by first determining the tool constants and optimal parameters prior to logging, using the FIR/CPMG sequence, measure the results, and transform the results into appropriate logs over a length of a borehole.

There have been disclosed and illustrated herein NMR pulse sequences which have advantageous use in conjunction with borehole tools. While particular embodiments have been presented, it is not intended that the invention be limited thereto, as it is intended that the invention be broad in scope and that the specification be read likewise. In particular, while certain equations have been set forth to describe the physics of NMR in the borehole, and the signal received by a borehole tool, those skilled in the art will recognize that different equations could be used as a model. Thus, the use of the particular equations set forth is intended to be illustrative rather than limiting. Similarly, other borehole tools for conducting the pulse sequence and measurements could suffice. The invention is intended to encompass determination of any formation characteristics where the characteristics can be related to the NMR determinations.

It should also be appreciated by those skilled in the arts that the waiting-inversion-recovery scheme of the FIR/CPMG sequence of U.S. Pat. No. 5,023,551 can be used. The FIR/CPMG sequence is an inversion sequence in which recovery time $\tau_i$ is another timing parameter of the pulse sequence which can be varied to yield a gas attribute of an earth formation. Additionally, advantageous results can be obtained where the waiting times of the FIR/CPMG sequence are reduced to the zero limit. The resulting pulse sequence may then be described as saturation recovery/ CPMG which is defined according to $$[\tau i - 90 - (t_{cp} - 180 - t_{cp} - echo)j]_i$$

and with echo amplitudes $$f_{ij} = M_o(1 - e^{\tau_i/T1})_e^{2t_{cp}j/T2}$$

for the single exponential model. Analogous expressions for the stretch exponential and multi-exponential models will be apparent to those skilled in the art. With saturation recovery/ CPMG, the recovery times, as well as the number of experiments (i.e., number of recovery times) and number of echoes in the CPMG sequence are preferably optimized.

In light of the above, it will be apparent to those skilled in the art that other changes and modifications may be made to the invention as described in the specification without departing from the spirit and scope of the invention as so claimed.

The invention can be implemented with an NMR wireline tool suspended from a cable into a borehole. See U.S. Pat. No. 5,055,787 to Kleinberg et al., for example. The invention can also be implemented with an NMR logging-while-drilling tool mounted to a drill string in a borehole. See U.S. patent application Ser. No. 07/922,254 to Kleinberg, et al., for example. With either type of tool, the pulse sequence can be altered as describe in this application. Also, each tool could house two sets of magnets, RF coil, etc. for separately performing NMR measurements, each set operating at a pulse sequence which is different from the other. Additionally, two tools of one type could be connected in series such that one tool in the series operates at a pulse sequence which is different from that of the other tool.

We claim:

1. A method for evaluating an earth formation using a nuclear magnetic resonance (NMR) tool, the steps comprising:

producing a static magnetic field in the formation;

producing an oscillating magnetic field in the formation according to a pulse sequence having a timing parameter;

providing a non-uniform magnetic field gradient;

varying the timing parameter of the pulse sequence;

receiving resulting signals induced in the formation; and indicating a gas attribute of the formation based on the received signals.

2. A method for evaluating an earth formation using a nuclear magnetic resonance (NMR) tool, the steps comprising:

producing a static magnetic field in the formation;

producing an oscillating magnetic field in the formation according to a pulse sequence having at least one of the SET: {waiting time, recovery time, echo spacing, and pulse spacing};

providing a non-uniform magnetic field gradient;

varying at least one of the SET of a subsequent pulse sequence;

receiving resulting signals induced in the formation; and indicating a gas attribute of the formation discernible in response to varying at least one of the set.

3. A method for evaluating an earth formation using a nuclear magnetic resonance (NMR) too, the step comprising:

producing a static magnetic field in the formation;

producing an oscillating magnetic field in the formation according to a varying pulse sequence;

providing a non-uniform magnetic field gradient;

receiving resulting signals induced in the formation; and indicating a gas attribute of the formation based on the received signals.

4. A method for making nuclear magnetic resonance measurements of an earth formation, the steps comprising:

producing a static magnetic field in the formation;

producing an oscillating magnetic field in the formation according to a pulse sequence;

providing a non-uniform magnetic field gradient;

varying the pulse sequence; and receiving resulting signals induced in the formation which indicate a gas attribute of the formation.

5. A method for indicating an attribute of a volume of a formation, using a nuclear magnetic resonance tool in a borehole in the formation, the steps comprising:

producing with the tool a static magnetic field in the volume of the formation;

producing with the tool an oscillating magnetic field in the volume of the formation according to pulse sequences, wherein a variable parameter determines the pulse sequences;

providing a non-uniform magnetic field gradient;

varying the parameter of at least one pulse sequence to get a gas attribute of the volume of the formation; and receiving with the tool signals induced in the volume of the formation, the induced signals indicating the gas attribute of the volume of the formation.

6. A method for indicating an attribute of an earth formation using a nuclear magnetic resonance tool, the steps comprising:

producing a static magnetic field in the formation;

producing an oscillating magnetic field in the formation according to at least a first pulse sequence having a first timing pattern, and a second pulse sequence having a second timing pattern different from the first timing pattern;

providing a non-uniform magnetic field gradient;

receiving resulting signals induced in the formation in response to the first and second pulse sequences; and indicating a gas attribute of the formation based on the received, induced signals.

7. The method of claim 6, comprising:

using the gas attribute in determining porosity of the formation.

8. The method of claim 6, comprising:

using the gas attribute to indicate gas saturation of the formation.

9. The method of claim 6, comprising:

using the gas attribute to indicate the chemical composition of gas in the formation.

10. A method for evaluating an earth forming using a nuclear magnetic resonance (NMR) tool, the steps comprising:

producing a static magnetic field in the formation;

producing an oscillating magnetic field in the formation according to pulse sequences having a waiting time before an initial pulse of one sequence;

providing a non-uniform magnetic field gradient;

varying the waiting time of pulse sequences;

receiving resulting signals in induced in the formation; and indicating a gas attribute of the formation based on the received signals.

11. A method for evaluating an earth formation using a nuclear magnetic resonance (NMR) tool, the steps comprising:

producing a static magnetic field in the formation;

producing an oscillating magnetic field in the formation according to a pulse sequence having at least one of the SET: {waiting time, recovery time, echo spacing, and pulse spacing};

providing a non-uniform magnetic field gradient;

varying the at least one of the SET of a subsequent pulse sequence;

receiving resulting signals induced in the formation; and indicating a gas attribute of the formation discernible in response to varying at least one of the SET using spin lattice (T1) relaxation time.

12. A method for indicating an attribute of a volume of a formation, using a nuclear magnetic resonance tool in a borehole in the formation, the steps comprising:

producing with the tool a static magnetic field in the volume of the formation;

producing with the tool an oscillating magnetic field in the volume of the formation according to pulse sequences, wherein a waiting time precedes the pulse sequences, providing a non-uniform magnetic field gradient;

varying the waiting time of at least on pulse sequence to get a gas attribute of the volume of the formation; and receiving with the tool signals induced in the volume of the formation, the induced signals indicating the gas attribute of the volume of the formation.

13. A method for indicating an attribute of an earth formation using a nuclear magnetic resonance tool, the steps comprising:

producing a static magnetic field in the formation;

producing an oscillating magnetic field in the formation according to at least a first pulse sequence having a first waiting time, and a second pulse sequence having a second waiting time different from the first waiting time;

providing a non-uniform magnetic field gradient;

receiving resulting signals induced in the formation in response to the first and second pulse sequences; and indicating a gas attribute of the formation based on the received, induced signals.

14. A method for measuring an indication of an attribute of a volume of earth formation with a borehole tool having means for producing static magnetic fields in a volume of a formation, means for producing oscillating magnetic fields in a volume of a formation, and means for measuring an induced magnetic signal, said method comprising: a) producing a static magnetic field in said volume of formation; b) producing oscillating magnetic fields according to a pulse sequence $$[W_i\text{--}90\text{--}(t_{cp}\text{--}180\text{--}t_{cp}\text{--}echo)_j]_i$$

where j=1, 2, ... J, and J is the number o echoes collected in a single Carr-Purcell-Meiboom-Gill (CPMG) sequence, where i=1, ... I, and I is the number of waiting times used in the pulse sequence, where $W_i$ are waiting times before a CPMG sequence, and where $t_{cp}$ is the Carr-Purcell spacing, in order to induce signals in said volume which are receivable by said tool in said borehole; c) providing a non-uniform magnetic field gradient; d) receiving with said tool said induced signals, and determining a gas characteristic of the volume of earth formation.

15. A method according to claim 14, wherein: said step of determining an indication of an attribute of the formation comprises using at least a value for a spin-lattice relaxation time (T1) of the formation from the induced signals.

16. A method according to claim 15, wherein:

said induced signals comprise at least CPMG echoes, and said step of measuring said induced signals comprises integrating at least portions of said CPMG echoes.

17. A method according to claim 16, further comprising: determining a first value proportional to an equilibrium value of longitudinal magnetization, determining the porosity of said formation according to a second relationship which relates the first value to porosity.

18. A method for measuring an indication of an attribute of a volume of earth formation with a borehole tool, said method comprising:

a) producing a static magnetic field in said volume of formation;

b) producing oscillating magnetic fields according to a pulse sequence $$[W_i\text{--}90\text{--}(t_{cp}\text{--}180\text{--}t_{cp}\text{--}echo)_j]_i$$

where j=1, 2, ... J, and J is the number of echoes collected in a single Carr-Purcell-Meiboom-Gill (CPMG) sequence, where i=1, ... I, and I is the number of recovery times in the pulse sequence, where $W_i$ are recovery times, and where $t_{cp}$ is the Carr-Purcell spacing, in order to induce signals in said volume which are measurable by said tool in said borehole;

c) providing a non-uniform magnetic field gradient; and, d) measuring with said tool said induced signals.

19. An apparatus for evaluating an earth formation using a nuclear magnetic resonance (NMR) tool comprising:

means for producing a static magnetic field in the formation;

a means for producing an oscillating magnetic field in the formation according to a pulse sequence having a timing parameter;

a means for providing a non-uniform magnetic field gradient;

a means for varying the timing parameter of the pulse sequence;

a means for receiving resulting signals induced in the formation; and a means for determining a gas attribute of the formation based on the received signals.

20. An apparatus for evaluating an earth formation using a nuclear magnetic resonance (NMR) tool, comprising:

a means for producing a static magnetic field in the formation;

a means for producing an oscillating magnetic field in the formation according to a pulse sequence having at least one of the SET: {waiting time, recovery time, echo spacing, and pulse spacing};

a means for providing a non-uniform magnetic field gradient;

a means for varying the at least one of the SET of a subsequent pulse sequence;

a means for receiving resulting signals induced in the formation; and a means for indicating a gas attribute of the formation discernible in response to varying at least one of the SET.

21. An apparatus for indicating an attribute of a volume of a formation, using a nuclear magnetic resonance tool in a borehole in the formation, comprising:

a means for producing with the tool a static magnetic field in the volume of the formation;

a means for producing with the tool an oscillating magnetic field in the volume of the formation according to pulse sequences, wherein a variable parameter determines the pulse sequences, a means for providing a non-uniform magnetic field gradient;

a means for varying the parameter of at least one pulse sequence to get a gas attribute of the volume of the formation, and a means for receiving with the tool signals induced in the volume of the formation, the induced signals indicating the gas attribute of the volume of the formation.

22. An apparatus for indicating an attribute of an earth formation using a nuclear magnetic resonance tool, comprising:

a means for producing a static magnetic field in the formation;

a means for producing an oscillating magnetic field in the formation according to at least a first pulse sequence having a first timing pattern, and a second pulse sequence having a second timing pattern different from the first timing pattern;

a means for providing a non-uniform magnetic field gradient;

a means for receiving resulting signals induced in the formation in response to the first and second pulse sequences; and a means for indicating a gas attribute of the formation based on the received, induced signals.

23. The method of claim 1, including evaluating the formation while drilling a borehole into the formation.

24. A method for characterizing a parameter of an earth formation using a nuclear magnetic resonance (NMR) tool, the steps comprising:
  producing a static magnetic field in the formation;
  producing an oscillating magnetic field in the formation according to a pulse sequences having a timing parameter;
  providing a non-uniform magnetic field gradient;
  varying the timing parameter of the pulse sequences;
  receiving resulting first signals induced in the formation;
  producing second signals indicating a gas attribute of the formation and based on the received first signals; and
  characterizing the parameter of the earth formation using the second signals.

25. A method for evaluating an earth formation using a nuclear magnetic resonance (NMR) tool, the steps comprising:
  producing a static magnetic field in the formation;
  producing an oscillating magnetic field in the formation according to a pulse sequence having at least one of the SET: {waiting time, recovery time, echo spacing, and pulse spacing};
  providing a non-uniform magnetic field gradient;
  varying at least one of the SET of a subsequent pulse sequence;
  receiving resulting signals induced in the formation; and
  indicating a gas attribute of the formation discernible in response to varying at least one of the SET while drilling a borehole into a formation.

26. A method for characterizing a parameter of an earth formation using a nuclear magnetic resonance (NMR) tool, the steps comprising:
  producing a static magnetic field in the formation;
  producing an oscillating magnetic field in the formation according to a pulse sequence having a timing parameter;
  providing a non-uniform magnetic field gradient;
  varying the timing parameter of the pulse sequence;
  receiving resulting first signals induced in the formation;
  producing second signals while drilling a borehole into the formation, such that the second signals are based on the received first signals; and
  characterizing the parameter of the earth formation using the second signals.

27. A method according to any of claims 1–6, 10–14, 18, or 24–26 further comprising the step of obtaining a distribution of relaxation times.

28. An apparatus according to any of claims 19–22, further comprising a means for obtaining a distribution of relaxation times.

29. A method for evaluating an earth formation using a nuclear magnetic resonance (NMR) tool, the steps comprising:
  producing a static magnetic field in the formation;
  producing an oscillating magnetic field in the formation according to a pulse sequence having at least one of the SET: {waiting time, recovery time, echo spacing, and pulse spacing};
  obtaining a distribution of relaxation times;
  varying at least one of the SET of a subsequent pulse sequence;
  receiving resulting signals induced in the formation; and
  indicating a gas attribute of the formation discernible in response to varying at least one of the set.

30. A method according to claim 29, further comprising the step of providing a non-uniform magnetic field gradient.

31. An apparatus for evaluating an earth formation using a nuclear magnetic resonance (NMR) tool, comprising:
  a means for producing a static magnetic field in the formation;
  a means for producing an oscillating magnetic field in the formation according to a pulse sequence having at least one of the SET: {waiting time, recovery time, echo spacing, and pulse spacing};
  a means for obtaining a distribution of relaxation times;
  a means for varying the at least one of the SET of a subsequent pulse sequence;
  a means for receiving resulting signals induced in the formation; and
  a means for indicating a gas attribute of the formation discernible in response to varying at least one of the SET.

32. An apparatus according to claim 31, further comprising a means for providing a non-uniform magnetic field gradient.

* * * * *